US006391948B1

(12) United States Patent
Clark et al.

(10) Patent No.: US 6,391,948 B1
(45) Date of Patent: May 21, 2002

(54) TRIAZINE COMPOUNDS AND USE THEREOF

(75) Inventors: Gregory D. Clark, St. Paul; Frederick E. Behr, Woodbury; Gary P. Roberts, Stillwater; Steven J. Vander Louw; Gregory K. Hall, both of Woodbury, all of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/461,153

(22) Filed: Dec. 14, 1999

(51) Int. Cl.$^7$ .................... C08K 5/3492; C07D 251/00
(52) U.S. Cl. .................. 524/101; 544/221; 544/222; 428/426; 428/496; 428/535
(58) Field of Search .................. 524/101; 544/221, 544/222; 428/426, 496, 535

(56) References Cited

U.S. PATENT DOCUMENTS

| | | | |
|---|---|---|---|
| 2,803,656 A | 8/1957 | Ahlbrecht et al. | 260/556 |
| 3,128,272 A | 4/1964 | Wear et al. | 260/249.6 |
| 3,321,445 A | 5/1967 | Lazerte et al. | 260/75 |
| 3,471,518 A | 10/1969 | Hager et al. | 260/345.9 |
| 3,598,852 A | 8/1971 | Berger | 260/448.2 |
| 3,615,739 A * | 10/1971 | Versanyi | 106/10 |
| 3,821,218 A | 6/1974 | Berger | 260/248 |
| 3,847,916 A | 11/1974 | Kim et al. | 260/248 |
| 3,849,450 A | 11/1974 | O'Rear et al. | 260/348 |
| 3,884,875 A | 5/1975 | Kim et al. | 260/46.5 |
| 3,899,563 A | 8/1975 | Oxenrider et al. | 264/211 |
| 3,971,373 A | 7/1976 | Braun | 128/146.2 |
| 4,100,324 A | 7/1978 | Anderson et al. | 428/288 |
| 4,215,205 A | 7/1980 | Landucci | 525/331 |
| RE30,782 E | 10/1981 | van Turnhout | 264/22 |
| 4,375,718 A | 3/1983 | Wadsworth et al. | 29/592 |
| RE31,285 E | 6/1983 | van Turnhout et al. | 55/155 |
| 4,426,466 A | 1/1984 | Schwartz | 523/455 |
| 4,429,001 A | 1/1984 | Kolpin et al. | 428/283 |
| 4,468,527 A | 8/1984 | Patel | 564/96 |
| 4,540,497 A | 9/1985 | Chang et al. | 252/8.8 |
| 4,566,981 A | 1/1986 | Howells | 252/8.8 |
| 4,588,537 A | 5/1986 | Klaase et al. | 264/22 |
| 4,592,815 A | 6/1986 | Nakao | 204/165 |
| 4,619,976 A | 10/1986 | Morris et al. | 525/439 |
| 4,835,300 A | 5/1989 | Fukui et al. | 560/25 |
| 4,843,134 A | 6/1989 | Kotnour et al. | 526/318.4 |
| 5,025,052 A | 6/1991 | Crater et al. | 524/104 |
| 5,145,727 A | 9/1992 | Potts et al. | 428/198 |
| 5,149,576 A | 9/1992 | Potts et al. | 428/198 |
| 5,414,111 A * | 5/1995 | Kirchner | 560/357 |
| 5,451,622 A | 9/1995 | Boardman et al. | 524/100 |
| 5,496,507 A | 3/1996 | Angadjivand et al. | 264/423 |
| 5,565,564 A * | 10/1996 | Kirchner | 544/221 |
| 5,908,598 A | 6/1999 | Rousseau et al. | 264/344 |

FOREIGN PATENT DOCUMENTS

| | | |
|---|---|---|
| EP | 0103752 | 3/1984 |
| JP | 58-190840 | 7/1983 |
| WO | WO 96/11981 | 4/1996 |
| WO | WO 96/22356 | 7/1996 |
| WO | WO 99/26992 | 6/1999 |

OTHER PUBLICATIONS

Mares, F., et al., "Modification of Fiber Surfaces by Monomeric Additives, Part I : Extrusion Techniques," *Textile Research Journal*, vol. 47, No. 8, pp. 551–561.

Mares, F., et al., "Modification of Fiber Surfaces by Monomeric Additives, Part II : Absorption of Fluorocarbon Additives by Polyethylene Terephthalate", *Textile Research Journal*, vol. 48, No. 4, pp. 218–229.

Griffith, J., "Nontoxic Alternatives to Antifouling Paints," *Journal of Coatings Technology*, vol. 59 (755), 1987, pp. 113–119.

Beca, A., et al., "Ease of Removal of Barnacles from Various Polymeric Materials," *Biotechnical and Bioengineering*, vol. 26, 1984, pp. 1245–1251.

Lindner, "Low Surface Free Energy Approach In The Control of Marine Biofouling," *Biofouling*, Hardwood Academic Polyurethane Publishers, vol. 99, 1992, pp. 193–205.

*Polymer Interface and Adhesion*, Marcel Dekker Inc., 1982., p. 181.

*Modern Approaches to Wettability Theory and Application*, Plenum Press, 1992, p. 332–333.

D. Rittshcof et al, *Biofouling*, vol. 6, 1992, pp. 181–192.

H.C. Fielding, "Organofluorine Chemicals and Their Industrial Applications", R.E. Banks, Ed., Society of Chemical Industry, 1979, pp. 214–234.

Van Wente et al., "Manufacture of Super Fine Organic Fibers," Report No. 4364 of the Naval Research Laboratories, May 25, 1954.

C.N. Davies, "The Separation of Airborne Dust and Particles", Institution of Mechanical Engineers, London, Proceedings 1B, 1952.

Van Wente, "Superfine Thermoplastic Fibers", Industrial Engineering Chemistry, vol. 48, 1956, pp. 1342–1346.

Dow Corning's *Automotive Car Formulation Guide* form No. 25–653–94, formulation APF 310.

* cited by examiner

*Primary Examiner*—Kriellion A. Sanders
(74) *Attorney, Agent, or Firm*—Kent S. Kokko

(57) ABSTRACT

The invention describes fluorochemical triazine compounds, compositions containing the fluorochemical triazine compounds, the process for preparing the fluorochemical compounds and compositions, substrates treated with the fluorochemical compounds, melt extrusion of fibers and films containing the fluorochemical compounds and compositions, and coating, polish and marine antifouling compositions to provide oil and water repellency to substrates.

31 Claims, No Drawings

TRIAZINE COMPOUNDS AND USE THEREOF

This invention relates to fluorochemical triazine compounds, compositions containing the fluorochemical triazine compounds, the process for preparing the fluorochemical compounds and compositions, substrates treated with the fluorochemical compounds, melt extrusion of fibers and films containing the fluorochemical compounds and compositions, and coating, polish and marine antifouling compositions to provide oil and water repellency to substrates.

Organofluorine compounds or fluorochemicals are substances containing portions that are fluorocarbon in nature and have properties such as hydrophobicity, oleophobicity, and chemically inertness, and portions that are organic or hydrocarbon in nature and which may be chemically reactive in organic reactions. Some fluorochemicals are familiar to the general public, such as SCOTCHGARD™ brand carpet protector, which imparts oil and water repellency and stain- and soil-resistance to carpet. Other fluorochemicals have other industrial uses, such as reducing the surface tension of liquids, reducing evaporation and inflammability of volatile organic liquids, and improving the leveling of organic polymer coatings.

The use of various fluorochemical compositions on fibers and fibrous substrates, such as textiles, paper, and leather, to impart oil and water repellency is known; see, for example, Banks, Ed., Organofluorine Chemicals and Their Industrial Applications, Ellis Horwood Ltd., Chichester, England, 1979, pp. 226–234. Such fluorochemical compositions include, for example, fluorochemical guanidines (U.S. Pat. No. 4,540,497, Chang et al.), compositions of cationic and non-cationic fluorochemicals (U.S. Pat. No. 4,566,981, Howells), compositions containing fluorochemical carboxylic acid and epoxidic cationic resin (U.S. Pat. No. 4,426,466, Schwartz), fluoroaliphatic carbodiimides (U.S. Pat. No. 4,215,205, Landucci), and fluoroaliphatic alcohols (U.S. Pat. No. 4,468,527, Patel).

Fluorochemical compositions can be applied to various fibrous substrates by methods which include, for example, spraying, padding, and finish bath immersion. Textile fibers and yarns can also be treated by incorporation of the fluorochemical in fiber spin finishes and by melt extrusion of a blend of a synthetic organic fiber-forming polymer and a fluorochemical composition. Such melt extrusion is described, for example, by Mares, F., et al., "Modification of Fiber Surfaces by Monomeric Additives, Part I: Extrusion Techniques," Textile Research Journal, Vol. 47, No. 8, pp. 551–561 and Mares, F., et al., "Modification of Fiber Surfaces by Monomeric Additives, Part II: Absorption of Fluorocarbon Additives by Polyethylene Terephthalate", Textile Research Journal, Vol. 48, No. 4, pp. 218–229, and in U.S. Pat. No. 3,899,563 (Oxenrider et al.)

Fluorochemical triazine compounds, and processes for preparing the same have been described, for example, in U.S. Pat. No. 3,128.272 (Wear et al.) which describes compounds of the formula:

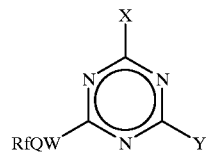

where X and Y are amino or hydrazino radicals, Rf is a perfluorinated alkyl radical and QW is a linking group. The compounds may be reacted with formaldehyde to yield polymethylol derivatives, which in turn may be condensed to thermosetting crosslinked polymeric products.

SUMMARY OF THE INVENTION

This invention provides fluorochemical triazine compounds comprising fluoroaliphatic radical-containing, tris thia-, aza- or oxa-alkylene triazine compounds, said compounds comprising one or more triazine moieties of the formula,

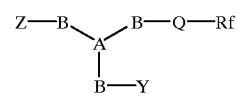

Where A is a triazine ring of the formula

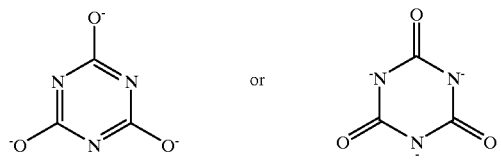

each B is an oxalkylene or thiaalkylene moiety,
each Q is a divalent linking group,
$R_f$ is a fluorinated aliphatic group,
Y is a functional group capable of further reaction, and
Z is —Q—Rf or Y.

This invention further provides coating compositions comprising aqueous suspensions or emulsions, or organic solvent solutions, of the fluorochemical triazine compositions, which compositions are useful in the surface treatment of hard surfaces, such as glass, wood, stone, tile, grout, concrete, metal, fiberglass, plastics such as polyacrylates and polycarbonates, and the like to impart oil and water repellency and anti-soiling properties thereto. This invention further provides compositions comprising aqueous suspensions or emulsions, or organic solvent solutions, of the fluorochemical triazine compositions, which compositions are useful in the surface treatment of fibrous substrates, such as textile fibers (or filaments) during their manufacture, and useful also in the surface treatment of finished or fabricated fibrous substrates such as textiles, carpets, paper and leather, to impart oil and water repellency and anti-soiling properties thereto. The present invention also provides coated substrates comprising the cured coatings of this invention, applied to the substrate.

Advantageously, coatings of the present invention generally cure, under ambient condition and without heating, to a tack-free state in fifteen minutes or less and pass the "pen test" (described below) within 45 minutes.

This invention also provides fibers, films, and molded articles prepared by melt extrusion and molded articles prepared by, e.g., injection molding of a blend or mixture of (a) fiber- or film-forming synthetic organic polymers and (b) fluorochemical triazines which fibers, films, and molded articles have low surface energy, oil and water repellency, and anti-soiling properties.

DETAILED DESCRIPTION OF THE INVENTION

Two classes of fluoroaliphatic radical-containing triazine compounds of this invention can be represented by the Formulas I and II

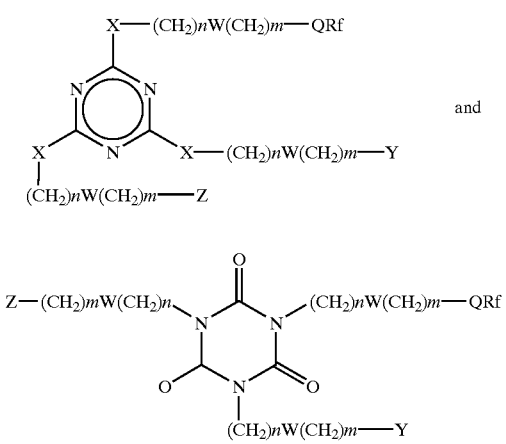

where each X is an oxygen or alkylamino of the formula —NR— each W is an oxygen, sulphur, alkylamino of the formula —NR'—, or urethane group of the formula —NR'—CO—O—, where R' is a lower alkyl or 1 to 4 carbon atoms, each n and m is independently an integer of from 1 to 20, preferably 2 to 12, Q is a linking group, Y is a reactive functional group, $R_f$ is a fluoroaliphatic radical, and Z is $R_f$ or Y.

In each of the above fluorochemical triazines of general Formulas I and II, where there are a plurality of $R_f$ and Y groups or moieties, each can be the same or different. Also Formulas II and I represent individual compounds or mixtures of compounds, for example, as they are obtained as products from reactions used in their preparation. In addition, small amounts of by-products, with and without the fluoroaliphatic radical $R_f$, and not represented by Formulas I and II, can also be present in small amounts in said mixtures or reaction products because of the reaction conditions involved in their preparation. The presence of such small amounts of by-products, generally less than 10 weight percent, does not affect the usefulness of the fluorochemical triazine mixtures or compounds of this invention.

The fluoroaliphatic radical, $R_f$, is a fluorinated, stable, inert, non-polar, preferably saturated, monovalent moiety which is both oleophobic and hydrophobic. It can be straight chain, branched chain, or, if sufficiently large, cyclic, or combinations thereof, such as alkylcycloaliphatic radicals. Though not preferred, the skeletal chain in the fluoroaliphatic radical can include catenary oxygen, hexavalent sulfur, and/or trivalent nitrogen hetero atoms bonded only to carbon atoms of the skeletal chain, such hetero atoms providing stable linkages between fluorocarbon portions of $R_f$ not interfering with the inert character of the $R_f$ radical.

While $R_f$ can have a large number of carbon atoms, compounds where $R_f$ is not more than 20 carbon atoms will be adequate and preferred since large radicals usually represent a less efficient utilization of fluorine than is possible with smaller $R_f$ radicals of less than 20 carbon atoms. Generally $R_f$ will have 3 to 20 carbon atoms, preferably 4 to about 12, and will contain 40 to 78 weight percent, preferably 50 to 78 weight percent, fluorine. The terminal portion of the $R_f$ group preferably has at least three fully fluorinated carbon atoms, e.g., $CF_3$ $CF_2$ $CF_2$—, and the preferred compounds are those in which the $R_f$ group is fully or substantially completely fluorinated.

The fluoroaliphatic radical, $R_f$, is bonded to the aza-, thia- or oxa-alkylene moiety by linking group, Q. Each Q may comprise a hetero atom-containing group, e.g., a group containing divalent sulfur or oxygen, or nitrogen (—NR—), (where R is a lower alkyl group), a covalent bond, an organic group or a combination of such groups, examples of which are divalent aliphatic, i.e., —$CH_2$—, —$CH_2CH_2$—, and —$CH_2$ $CH_2CH_2$—, divalent aromatic, oxy, thio, carbonyl, sulfone, sulfoxy, —N($CH_3$)—, sulfonamido, carbonamido, sulfonamidoalkylene, e.g., —$SO_2NR(CH_2)_x$—, where x is 1 to 6 and R is lower alkyl having 1 to 4 carbon atoms, carbonamidoalkylene, carbonyloxy, urethane, e.g., —$CH_2CH_2OCONH$—, and urylene, e.g., —NHCONH—. The linkage Q for a specific fluorochemical triazine will be dictated by the ease of preparation of such a compound and the availability of necessary precursors thereof. However, the Q group is preferably free of said active hydrogen atoms.

The fluorochemical triazines of the invention contain a functional group Y capable of further reaction with a substrate, a binder composition or other molecules of fluorochemical triazine. The functional groups useful include those nucleophilic or electrophilic groups capable of undergoing a nucleophilic or electrophilic displacement reaction, or those groups having carbon-carbon unsaturation and capable of undergoing free radical polymerization.

Functional groups that may undergo further displacement reactions include hydroxyl, amino, azlactyl, oxazolinyl, 3-oxobutanoyl (i.e., acetoacetyl), carboxyl, ester, isocyanato, epoxy, aziridinyl, acyl halide, vinyloxy, silane, silanol or anhydride groups. Preferred functional groups are the silane and silanol groups having the structure —Si(OR) 3, where each R is an H or lower alkyl group of 1 to 4 carbon atoms. As used herein, "silane" will refer to both alkyl silanes and silanols. Useful functional groups that may undergo free radical polymerization include carbon-carbon double and triple bonds, including alkanes, alkenes, (meth) acrylates and vinyl ethers. Especially useful are those containing terminal double bonds of the structure —CH=$CH_2$ and —CO—CH=$CH_2$.

The choice of a particular functional group depends on both the binder resin (if any), solvent (if any) and substrate. For example, when using a melamine, urea-formaldehyde or phenolic resin binder, functional groups such as amino, ester, isocyanato, acid halide and epoxy are especially preferred. When using epoxy resins or acrylic resins, any nucleophilic functional group is preferred. When using alkyd resins or polyesters, hydroxyl or ester functional groups are preferred. The weight ratio of the binder to the fluorochemical triazine is typically in the range of 95:5 to 60:40, preferably 90:10 to 70:30. It is preferred for reasons of cost that the amount of triazine be kept to a minimum, while still providing the coating with good stain and solvent resistance. Further, it has been found that the solvent resistance begins to diminish at triazine levels below 10 wt.%.

Where two functional groups are present on the fluorochemical triazine, the functional groups may be the same or different. The functional groups may also be selected to be co-reactive with each other to produce dimers, trimers, oligomers and polymers. For example, the functional groups selected may be hydroxyl and acid halide to produce dimers (and higher) linked through an ester moiety. Trialkoxy silane functional groups are co-reactive with each other in the presence of acid catalysts such as titanium isopropoxide to form polysiloxanes having pendant fluorochemical triazine moieties. Additionally, the functional groups may be selected to be co-reactive with polyfunctional co-reactive compounds. The polyfunctional compounds have at least two functional groups, which may be the same or different as described above for the Y group. Examples of useful polyfunctional compounds are polyols such as ethylene glycol and poly(ethylene oxide) diols, polyamines such as ethylene diamine or poly(alkylene oxide) diamines, polyacids such as adipic acid, silanes and polysilanes and the like. Especially preferred are fluorinated polyfunctional compounds such as fluorine containing diols such as $R_fQN(C_nH_{2n}OH)_2$, wherein Rf, Q and n are as previously defined in Formulas I and II. Useful fluorinated polyhydroxy compounds are disclosed in U.S. Pat. No. 3,321,445 (LaZerte et al), incorporated herein by reference. Illustrative compounds include:

1,2-propanediol-3-(N-ethyl perfluorooctanesulfonamide);

1,5-hexanediol-6-(N-ethyl perfluorooctanesulfonamide);

1,2-propanediol-3-(N-propyl perfluoroethanesulfonamide);

1,2-propanediol-3-(N-ethyl perfluorobutylcyclohexanesulfonamide); 1,5-hexanediol-6-(N-ethyl perfluorobutylcyclohexanesulfonamide);

1,2-propanediol-3-(N-isopropyl perfluorooctanesulfonamide);

1,2,3-butanetriol-4,(N-ethyl perfluorooctanesulfonamide);

$C_8F_{17}SO_2N(C_2H_5)CH_2CH(OH)CH_2OC_6H_4C(CH_3)_2C_6H_4OCH_2CH(OH)CH_2OH$;

$C_8F_{17}SO_2N(C_2H_5)CH_2CH(OH)CH_2OCH_2CH(OH)CH_2OH$

Examples of useful fluorine-containing diamines include but are not limited to those selected from the group consisting of fluorinated derivatives of 4,4'-methylene bis(o-chloroaniline)(MOCA or MBOCA), 2,5-diethyl-2,4-toluene diamine (DETDA), 4,4'-methylene bis(3-chloro-2,6-diethylaniline)(MCDEA), propylene glycol bis(4,4'-aminobenzoate), 3,5-di(thiomethyl)-2,4-toluene diamine, methylene bis(4,4'-aniline)(MDA), ethyl-1,2-di(2-amino thiophenol), 4-chloro-3,5-diamino isobutylbenzoate, 1,2-diaminoethane, 1,4-diaminobutane, 1,6-diaminohexane, N,N'-dialkyl(methylene dianiline), N,N'-dialkyl(1,4-diaminobenzene), and mixtures thereof. Useful fluorine containing amines are described, for example in WO 99/26992.

Examples of useful fluorine containing dicarboxylic acids and corresponding anhydrides and acid chlorides include compounds represented by the structures:

$R_f(CH_2)_nSC(R)(COOH)CH(R)COOH$; $R_fCH_2)_nSCH(CH_2COOH)_2$;

$R_f(CH_2)SCH_2CH(COOH)CH(R)COOH$; where $R_f$ is defined for Formulas I and II, n=1–3, and R is H or lower alkyl. Illustrative compounds are $C_9F_{19}CH_2CH_2SCH(COOH)CH_2COOH$, the corresponding anhydride, and the corresponding acid chloride. Such compounds are described in U.S. Pat. No. 3,471,518, incorporated herein by reference.

Difunctional epoxide compounds are also useful. Examples of this type of compound are $(CF_3)_2COCHC_6H_4CHOC(CF_3)_2$ and $C_{10}F_{21}SO_2N(CH_2CHOCH_2)_2$. Such compounds are described for example in U.S. Pat. Nos. 3,849,450 and 5,025,052, incorporated herein by reference.

Such fluorochemical polyfunctional compounds may be reacted with functional groups "Y" (such as acid, acid halide, ester or isocyanate functional groups) to produce di-, tri- or tetrameric fluorochemical triazines having an additional pendant fluorochemical moiety. Such compounds have the general formula

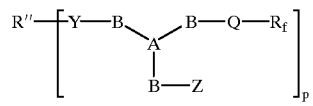

where Y, B, A, Q, $R_f$ and Z are as previously defined and R" is derived from a polyfunctional compound of functionality p, and p is a number from 2 to 4. R" is a aliphatic chain of 2 to 20 carbon atoms, which may contain catemary (i.e. in chain) ether atoms, and is preferably fluorinated. Preferably polyfunctional compounds have the general structure $R_f''(Y')_p$, where each Y' is a functional group co-reactive with the functional groups Y on the fluorochemical triazine, $R_f''$ is a fluoroaliphatic chain of 4 to 12 carbon atoms, $R_f''(Y')_p$ having a valency of p, and p is 2 to 4. Most preferably $R_f''(Y')_p$ contains a pendent perfluoroalkyl radical of 4 to 12 carbon atoms.

A salient feature of the compounds of the present invention is the divalent oxygen or sulfur atom in the oxa- or thia-alkylene moiety, which connect the triazine ring and the —Q—$R_f$ moiety. It has been found that the presence of this divalent sulfur or oxygen enhances the performance of coating derived from the compounds of the invention. In particular, the low surface energy properties of coating are enhanced by the presence of the oxa-alkylene or thia-alkylene moiety. While not wishing to be bound by theory, it is believed that the presence of this moiety confers greater conformational freedom on the fluoroalkyl radical, allowing it to orient itself at the surface of the coating, resulting in a greater concentration of fluorine at the surface. A preferred formula for the moiety —Q—Rf is —S—$(CH_2)_nR_f$, wherein n is an integer of 1 to 5

The fluorochemical triazine compounds of this invention can be prepared using known organic reactions e.g. from the addition of an oxygen or sulfur radical to an olefin, by a nucleophilic displacement or condensation reaction of an oxygen, nitrogen or sulfur nucleophile. These reaction may be illustrated as follows, starting with compounds of the general formula

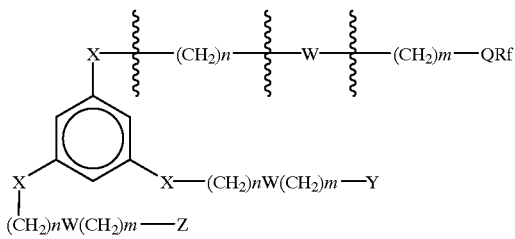

Such compounds are conveniently prepared by reactions making the bonds dissected with a wavy line as further illustrated below and as described in the Examples. Thus, when X is an oxygen, the compounds may be prepared by a nucleophilic displacement reaction of an alkoxide with a fluoroalkyl compound bearing a leaving group "Y" as shown, with the remaining two substituents on the triazine ring deleted for clarity:

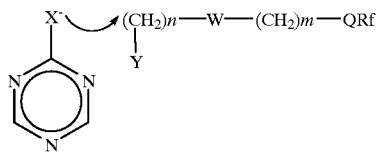

Similarly, one may prepare the compounds of the invention by the following displacement reactions:

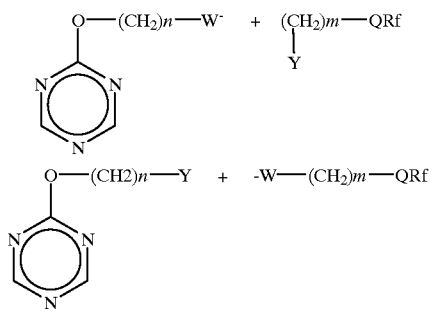

Alternatively, the compounds are conveniently prepared by the addition of an oxygen or sulfur radical to a carbon-carbon double bond. The free radicals are readily prepared from the corresponding hydroxyl- or thiol-containing compounds by means of a free-radical initiator. Useful initiators include either thermally or photochemically activated initiators. Suitable thermally activated initiators include azo compounds such as 2,2'-azobis(isobutyronitrile), hydroperoxides such as tert-butyl hydroperoxide, and peroxides such as benzoyl peroxide. Suitable photochemically activated initiators include benzoin ethyl ether and 2,2-dimethoxy-2-phenyl acetophenone. The amount of initiator used is generally about 0.01% to about 5% by weight of the total composition.

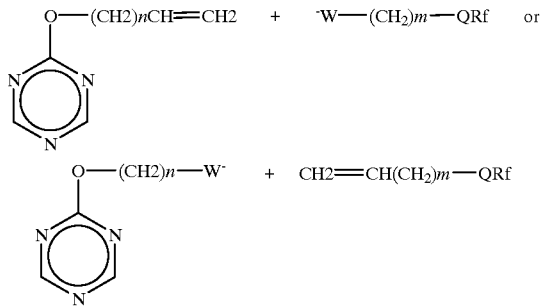

An especially useful and versatile procedure for preparing the fluorochemical triazine compounds is the free radical addition of a functional thiol compound to a triazine having a pendant unsaturated group, followed by addition of the fluorochemical moiety as shown below:

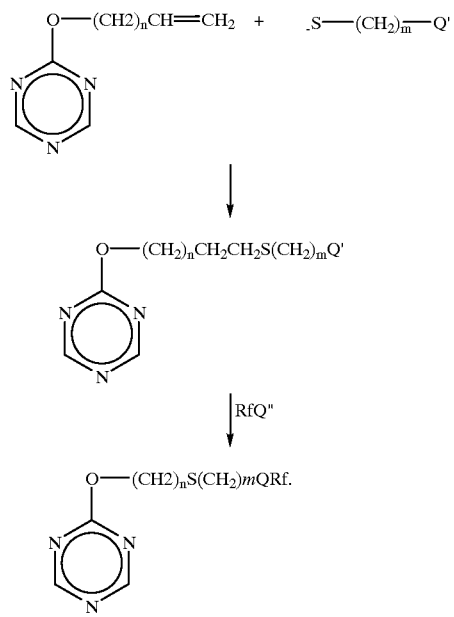

In the above Scheme, a functional thiol has a functional group Q' which reacts with a co-reactive functional group Q" to incorporate the fluorochemical moiety $R_f$ and produce the triazine compounds of the invention having a linking group Q.

Examples of such functionalized thiol compounds include 2-mercaptoethanol, mercaptoacetic acid, 2-mercaptobenzimidazole, 2-mercaptobenzoic acid, 2-mercaptobenzothiazole, 2-mercaptobenzoxazole, 3-mercapto-2-butanol, 2-mercaptoethanesulfonic acid, 2-mercaptonicotinic acid, 4-hydroxythiophen-3-mercapto-1, 2-propanediol, 1-mercapto-2-propanol, 2-mercaptopropionic acid, N-(2-mercaptopropionyl) glycine, 3-mercaptopropyltrimethoxysilane, 2-mercaptopyridine, 2-mercaptopyridine-N-oxide, 2-mercaptopyridinol, mercaptosuccinic acid, 2,3-mercaptopropanesulfonic acid, 2,3-dimercaptopropanol, 2,3-dimercaptosuccinic acid, cystine, cystine hydrochloride, cystine ethylester. Preferred functionalized chain-transfer agents include 2-mercaptoethanol, 3-mercapto-1,2-propanediol, 4-mercaptobutanol, 11-mercaptoundecanol, mercaptoacetic acid, 3-mercaptopropionic acid, 12-mercaptododecanoic acid, 2-mercaptoethylamine, 1-chloro-6-mercapto-4-oxahexan-2-ol, 2,3-dimercaptosuccinic acid, 2,3-dimercaptopropanol, 3-mercaptopropyltrimethoxysilane, 2-chloroethanethiol, 2-amino-3-mercaptopropionic acid, and compounds such as the adduct of 2-mercaptoethylamine and caprolactam.

It will be understood with respect to the above Schemes that the other substituents on the triazine ring may be added using similar reaction schemes. Additionally such reaction schemes may be used with the triazine ring having the structure

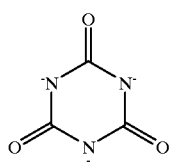

Generally the triazine rings are functionalized by sequential addition of the three subsituents on the triazine ring. It may be noted however, that the reaction schemes may lead to more that one site on the triazine site being functionalized and the Formulas I and II represent average formulas as result of the reactions employed. Consequently, the average substitution pattern may result in some ratio or fluorochemical groups to functional groups other than 1:2 or 2:1. For example, the fluorochemical triazine may contain an average of one-third of the sites substituted by fluoroalkyl groups and two-thirds silyl groups, for a 1:2 ratio, or the average may be ½ fluoroalkyl groups and ½ silyl groups, for a 1:1 ratio. Put another way, by way of illustration, each fluorochemical triazine may contain an average of 1.5 fluoroalkyl groups and 1.5 silyl groups per molecule.

Generally, the ratios of fluorochemical groups to functional groups can vary widely; from 3:1 to 1:3. When used as a coating for hard surfaces, or when used in a polish composition, it is preferred that the fluorochemical triazine compounds have a ratio of fluorochemical groups to functional groups in the range of from 1:1 to 1:3. With such substitutions it has been found that adhesion is improved, as result of reaction between the functional groups and the substrate or crosslinking between functional groups. When used in the treatment of textiles or as a polymer melt additive, it is preferred that the fluorochemical triazine compounds have a ratio of fluorochemical groups to functional groups in the range of from 2:1 to 1:1, to maximize the amount of fluorochemical.

The fluorochemical triazine compounds may be coated and cured neat, with or without additional solvent. The fluorochemical triazine coating composition may further comprise a binder. The binders are organic thermally or UV curable polymeric compositions that exhibit sufficient adhesion to a chosen substrate and are compatible with the fluorochemical triazine composition. By compatible it is meant that the triazine compositions are dissolvable or dispersible in the binder compositions prior to curing. Examples of such binders include: resinous binders such as phenolic resins, urethane resins, urea-formaldehyde resins, melamine and melamine-formaldehyde resins, epoxy resins, alkyd resins, amino resins and acrylate resins. Suitable binder may also include waxes and silicone oils to produce a coating composition suitable as an automobile or marine wax. The preferred materials for the binder are dependent on the substrate chosen. The functional group(s) of the fluorochemical triazine is generally chosen so as to be reactive with functional groups of the binder. For example, when an amino resin, such as a melamine resin, is chosen as the binder, the functional group of the fluorochemical triazine is chosen so as to be co-reactive with the amino or hydroxyl functional groups of the amino resin. Suitable functional groups "Y" may include nucleophilic functional group such as hydroxyl, amino or mercapto, or may include electrophilic functional groups such as isocyanates, acyl halides, epoxy or esters.

When the fluorochemical triazine has a silane functional group, the triazine may be blended with a silane functional oil or resin as a binder. The silane groups of the fluorochemical triazine and the silicone oil co-react to form Si—O—Si linkages to form a durable, fluorine-containing coating in a cured polysiloxane binder.

The fluorochemical triazine is added to a binder in amounts sufficient to impart the desired low surface energy properties, such as oil- and/or water-repellency, to the cured coating. Generally, the weight ratio of the binder to the fluorochemical triazine is in the range of 95:5 to 60:40, preferably 90:10 to 70:30. It is preferred for reasons of cost that the amount of fluorochemical triazine be kept to a minimum, while still providing the coating with desirable low surface energy properties.

If a more flexible coating is desired, a polyester polyol may be added to the coating composition. Relatively small concentrations of these materials can increase the flexibility of the cured coating without sacrificing hardness, can improve the adhesion of the cured coating to substrates and improve the film-forming properties of the coating. Typically, amounts of 1 to 20 percent of the total weight of the triazine and binder composition is necessary to improve coating flexibility.

Useful commercially available polyester polyols include those sold under the K-FLEX™ brand by King Industries of Norwalk, Connecticut. Useful commercially available polyester polyols include the K-FLEX™ brand by King Industries of Norwalk, Conn.

Solvents may be added to the curable coating composition to reduce the viscosity of the compositions, whether or not a binder resin is included. Examples of useful solvents include: lower alcohols; halogenated hydrocarbon solvents; ketones; aromatic solvents; fluorinated ethers in which one or more hydrogen atoms of an ether has been replaced by a fluorine atom; hydrofluorocarbon solvents (i.e., compounds having only carbon, fluorine and hydrogen atoms); and water. However if water is added to the coating composition, the functional group employed (Y) is preferably a hydrophilic functional group such as a carboxylate. The composition should be treated with an organic or inorganic base to neutralize any unreacted carboxylic acid groups and render the product more water-soluble or water-dispersible. Silane functional groups are also useful in preparing water-soluble or water-dispersible coating compositions. The silane functional group such as —$Si(OCH_3)_3$ may be added to water or to an organic solvent containing a small amount of water, The water will hydrolyze the silane to a silanol (—$Si(OH)_3$), rendering the fluorochemical triazine water-soluble or water-dispersible. The organic solvent, if used, may be removed from the aqueous solution or dispersion. The amount of solvent added to the composition is dependent upon the solids content or viscosity of the coating composition desired and it is well within the abilities of one of ordinary skill in the art to vary the amount of solvent and other coating composition components to achieve the desired result. Preferably the coating composition has a viscosity of from about 500 to 10,000 cps. In some cases, more aggressive solvents can be used to enhance the adhesion of the coating to certain substrates. For example, methyl ethyl ketone can enhance adhesion to vinyl substrates. Representative examples of useful organic solvents include ethanol, methanol, isopropanol, tert-butanol, chloroform, methylene chloride, toluene, benzene, xylene, trichloroethane, 1,2-dichloroethane, acetone and methyl ethyl ketone. The fluorinated ethers possess good solvent properties as well as exceptional chemical and thermal stability. Since they lack chlorine atoms, they have a zero ozone depletion potential and therefore do not contribute to global warming. A preferred class of fluorinated ethers are the alkoxy-substituted perfluorolkanes described in WO 96/22356.

The curable coating composition can be applied to a wide variety of substrates to impart abrasion resistance, solvent resistance, and repellency, as well as to impart anti-staining and anti-soiling characteristics to the surface. In general, the type of substrates that can be coated include both rigid and flexible substrates such as: plastics, glass, metal, wood and ceramics. Representative examples of substrates that can be coated with the coating composition include: lenses used in ophthalmic spectacles, sunglasses, optical instruments, illuminators, watch crystals, and the like; plastic window glazing; signs and decorative surfaces such as wallpaper and vinyl flooring; and composite or laminated substrates such as FORMICA™ brand sheeting or laminated flooring (e.g., PERGO™ brand flooring). Since coatings prepared from the curable coating composition can render metal surfaces resistant to soils, the optical properties of metal surfaces like those on decorative metal strips and mirrors can be preserved longer. The coating composition can make wood surfaces more resistant to food and beverage stains while providing a lustrous appearance. In addition, the coating composition can be applied as a protective coating on aircraft (in deicing wings), on boat hulls and other surfaces exposed to marine environment as anti-fouling coatings, as automotive polish, as automotive topcoat, and as automotive transit coating. It can also be used on concrete, fishing line, medical surfaces, siding, sinks, showers, vinyl flooring, and wallcovering; and can be used in food release, mold release, adhesive release applications, and the like.

The curable coating composition can be applied to a substrate using any conventional technique. For example, the composition can be brushed or sprayed (e.g., as an aerosol) onto a substrate, or the substrate can be immersed in the coating composition or can be spin-coated. When coating flat substrates, it is preferable to knife-coat or bar-coat the substrate to ensure uniform coatings.

The coating compositions can be applied to a substrate in any desired thickness. It has been found that coatings as thin as a few microns offer excellent abrasion resistance and low surface energy. However, thicker coatings (e.g., up to about 20 microns or more) can be obtained by applying a single thicker coating or by applying successive layers of the coating to the substrate. The latter can be done by applying a layer of the coating composition to the substrate and then drying without extensive curing, for example, by heating the coated substrate for about one minute at about 60° C. Successive layers of the coating can then be applied to dried, but uncured, coatings. This procedure can be repeated until the desired coating thickness is obtained and then the coated substrate is cured at elevated temperature to the desired level. It is particularly advantageous to cure the coating at elevated temperatures (i.e., greater than about 60° C.) in order to achieve the optimum water repellency properties.

The present invention provides a synthetic organic polymer composition comprising one or more of the fluorinated triazine compounds of the invention and a melt-processible synthetic organic polymer. The compounds of the invention are useful as polymer melt additives to impart desirable low surface energy properties to the melt-processible polymer. Useful polymers include both thermoplastic and thermoset polymers and include synthetic linear polyamides, e.g., nylon-6 and nylon-66, polyesters, e.g., polyethylene terephthalate, polyurethanes, epoxides, acrylics, polystyrenes and polyolefins, e.g., polyethylene and polypropylene. Thermoplastic polymers such as polyolefins are preferred. The resultant articles, due to the presence of the fluorochemical additive, have improved oil- and water-repellency, low surface energy and a resistance to soiling.

Thus, the fluorochemical triazines are also useful as melt additives to thermoplastic polymer melts from which blown microfibers are made for use in making non-woven fabrics having low surface energy, oil and water repellency and/or soiling resistance. The resin, such as polypropylene, used to form the melt blown microfibers should be substantially free from mobile polar and/or ionic species, contaminants and impurities and materials such as antistatic agents which could increase the electrical conductivity or otherwise interfere with the ability of the fibers to accept and hold electrostatic charges. When the fluorochemical triazine compounds of the invention are used as additives to melt blown microfibers, the additive is preferably present in amounts of about 0.2 to 10 weight percent, more preferably from 0.5 to 5 weight percent and most preferably 0.5 to 2 weight percent.

Shaped articles (e.g., fibers, films and molded or extruded articles) of this invention can be made, e.g., by blending or otherwise uniformly mixing the fluorochemical triazine and the solid synthetic polymer, for example by intimately mixing the oligomer with pelletized or powdered polymer, and melt extruding the mixture into shaped articles such as pellets, fibers, or films by known methods. The triazine can be mixed per se with the polymer or can be mixed with the polymer in the form of a "masterbatch" (concentrate) of the oligomer in the polymer. Masterbatches typically contain from about 10% to about 25% by weight of the fluorochemical triazine additive. Also, an organic solution of the triazine may be mixed with the powdered or pelletized polymer, the mixture dried to remove solvent, then melted and extruded into the desired shaped article. Alternatively, molten oligomer (as a compound(s) or masterbatch) can be injected into a molten polymer stream to form a blend just prior to extrusion into the desired shaped article.

When using thermoset resins, such as epoxy resins, urethanes and acrylates, the fluorochemical triazine may be mixed with the resin and cured by application of heat. Preferably such thermoset resins may be processed by reactive extrusion techniques such as are taught in U.S. Pat. No. 4,619,976 (Kotnour) and U.S. Pat. No. 4,843,134 (Kotnour) the disclosures of which are herein incorporated by reference.

The amount of fluorochemical triazine in the composition is that amount sufficient to produce a shaped article having a surface with the desired properties of oil and water repellency and/or soiling resistance. Preferably, the amount of oligomer will be that amount which provides from about 100 to 10,000 ppm fluorine, more preferably 200 to 5000 ppm, most preferably 400 to 3000 ppm fluorine, based on the weight of the shaped article.

After melt extrusion of a fiber, film or extruded article, an annealing step may be carried out to enhance oil and water repellency. Annealing apparently allows the fluorochemical triazine to migrate to the surface of the thermoplastic polymer with a resultant increase in repellency properties, reduced surface energy, improved solvent resistance and improved release properties. The fiber or film is annealed at a temperature and for a time sufficient to increase the amount of fluorochemical triazine at the surface. Effective time and temperature will bear an inverse relationship to one another and a wide variety of conditions will be suitable. Using nylon, for example, the annealing process can be conducted below the melt temperature at about 150° to 220° C. for a period of about 30 seconds to 5 minutes. In some cases, the presence of moisture during annealing, e.g., by using an autoclave to anneal, can improve the effectiveness of the fluorochemical triazine additive. The annealing method may also serve to reduce the amount of triazine necessary by maximizing fluorine content at the surface of the polymer.

The non-woven webs of fibers of thermoplastic olefinic polymer for use in this invention include non-woven webs manufactured by any of the commonly known processes for producing non-woven webs. For example, the fibrous non-woven web can be made by spunbonding techniques or melt-blowing techniques or combinations of the two. Spunbonded fibers are typically small diameter fibers which are formed by extruding molten thermoplastic polymer as filaments from a plurality of fine, usually circular capillaries of a spinneret with the diameter of the extruded fibers being rapidly reduced. Meltblown fibers are typically formed by extruding the molten thermoplastic material through a plurality of fine, usually circular, die capillaries as molten threads or filaments into a high velocity, usually heated gas (e.g. air) stream which attenuates the filaments of molten thermoplastic material to reduce their diameter.

Thereafter, the meltblown fibers are carried by the high velocity gas stream and are deposited on a collecting surface to form a web of randomly disbursed meltblown fibers. Any of the non-woven webs may be made from a single type of fiber or two or more fibers which differ in the type of thermoplastic olefinic polymer and/or thickness. Alternatively, sheath-core fibers can be extruded, containing different polymer compositions in each layer or containing the same polymer composition in each layer but employing the more expensive fluorochemical component in the outer sheath layer.

The melt blown polypropylene microfibers useful in the present invention can be prepared as described in Van Wente, A., "Superfine Thermoplastic Fibers," Industrial Engineering Chemistry, vol. 48, pp. 1342–1346 (1956) and in Report No. 4364 of the Naval Research Laboratories, published May 25, 1954, entitled "Manufacture of Super Fine Organic Fibers" by Van Wente et al. or from microfiber webs containing particulate matter such as those disclosed, for example, in U.S. Pat. No. 3,971,373 (Braun), U.S. Pat. No. 4,100,324 (Anderson) and U.S. Pat. NO. 4,429,001 (Kolpin et al.), which patents are incorporated herein by reference. Multilayer constructions of nonwoven fabrics enjoy wide industrial and commercial utility and include uses such as fabrics for medical gowns and drapes. The nature of the constituent layers of such multilayer constructions can be varied according to the desired end use characteristics, and can comprise two or more layers of melt-blown and spun-bond webs in may useful combinations such as described in U.S. Pat. Nos. 5,145,727 and 5,149,576, both descriptions of which are incorporated herein by reference. The filtering efficiency of a melt-blown microfiber web can be improved by a factor of two or more when the melt-blown fibers are bombarded as they issue from the orifices with electrically charged particles such as electrons or ions, thus making the fibrous web an electret. Similarly, the web can be made an electret by exposure to a corona after it is collected. Melt-blown polypropylene microfibers are especially useful, while other polymers may also be used such as polycarbonates and polyhalocarbons that may be melt-blown and have appropriate volume-resistivities under expected environmental conditions.

Any of a wide variety of constructions, especially multi-layer constructions such as SMS (spunbond/meltblown/spunbond) constructions, may be made from the above-described fibers and fabrics, and such constructions will find utility in any application where some level of hydrophobicity, oleophobicity (or other fluid repellency, such as to bodily fluids) is required. The fibers prepared from the synthetic organic polymer composition of the invention may be used in woven and nonwoven medical fabrics (such as drapes, gowns and masks), industrial apparel, outdoor fabrics (such as umbrellas, awnings, tents, etc), raincoats and other outdoor apparel, as well as home furnishings such as table linens and shower curtains, and in myriad other related uses.

Preferably, the filter media are annealed, i.e. heated for a sufficient time at a sufficient temperature to cause the fluorochemical triazine additive to bloom to the surface of the fibers. Generally, about 1 to 10 minutes at about 140 deg. C. is sufficient although shorter times may be used at higher temperatures and longer times may be required at lower temperatures.

Blown microfibers for fibrous electret filters of the invention typically have an effective fiber diameter of from about 2 to 30 micrometers, preferably from about 7 to 10 micrometers, as calculated according to the method set forth in Davies, C. N., "The Separation of Airborne Dust and Particles," Institution of Mechanical Engineers, London, Proceedings 1B, 1952.

The electret filter medium of the present invention preferably has a basis weight in the range of about 10 to 500 $g/m^2$, more preferably about 10 to 100 $g/m^2$. In making melt-blown microfiber webs, the basis weight can be controlled, for example, by changing either the collector speed or the die throughput. The thickness of the filter media is preferably about 0.25 to 20 mm, more preferably about 0.5 to 2 mm. The electret filter media and the polypropylene resin from which it is produced should not be subjected to any unnecessary treatment which might increase its electrical conductivity, e.g., exposure to gamma rays, ultraviolet irradiation, pyrolysis, oxidation, etc.

The melt-blown microfibers or fibrillated fibers of the electret filters of the invention can be electrostatically charged by a process described in U.S. Pat. No. Re. 30,782 (van Turnhout) or U.S. Pat. No. Re. 31,285 (van Turnhout) or by other conventional methods for charging or polarizing electrets, e.g., by a process of U.S. Pat. No. 4,375,718 (Wadsworth et al.); U.S. Pat. No. 4,588,537 (Klasse et al.); or U.S. Pat. No. 4,592,815 (Nakao). In general, the charging process involves subjecting the material to corona discharge or pulsed high voltage. Alternatively the fibers may be charged by impinging a jet or stream of water droplets, followed by drying to provide the web with filtration enhancing electret charge as described in U.S. Pat. No. 5,496,507 (Angadjirand et al.).

The triazine compounds of the invention are also useful in the surface treatment of fibrous substrates to impart improved oil and/or water repellency, and soil and/or stain release properties. Useful fibrous substrates which may be topically treated (surface treated) include natural textiles and fabrics such as cotton or wool and synthetic fabrics or textiles such as polyester or nylon, as well as paper and leather. Topical treatment can be done via immersion, spray, foam, kiss roll and metering. For example, the substrate can be immersed in a dispersion or solution of the fluorochemical triazine and agitated until it is saturated. The saturated substrate can then be run through a padder/roller to remove excess dispersion, dried in an oven at a relatively low temperature (e.g., 70° C.) for a time sufficient to remove the dispersion medium (e.g. solvents such as those used in the oligomerization reaction), and cured at a temperature and for a time sufficient to provide a cured treated substrate. This curing process can be carried out at temperatures between 40° C. and about 200° C. depending on the particular composition used. In general, a temperature of about 150° C.

for a period of about 10 minutes is suitable. The cured treated substrate can be cooled to room temperature and used as desired, e.g., incorporated or fashioned into a garment such as rainwear.

As used herein, the terms "fiber" and "fibrous" refer to particulate matter, generally thermoplastic resin, wherein the length to diameter ratio of the particulate matter is greater than or equal to about 10. Fiber diameters may range from about 0.5 micron up to at least 1,000 microns. Each fiber may have a variety of cross-sectional geometries, may be solid or hollow, and may be colored by, e.g., incorporating dye or pigment into the polymer melt prior to extrusion.

The fluorochemical triazine compounds may also be used to produce a polish composition, suitable for use in automotive and marine applications. Polish compositions of the invention comprise the fluorochemical triazine and a binder component, which may be a wax or a silicone oil. Useful waxes and silicone oils are described in Assignee's copending patent application U.S. Ser. No. 09/309,461 filed May 11, 1999, the disclosure of which is incorporated herein by reference. The triazine can be present in the polish composition of the present invention in any amount that provides useful water repellency, stain resistance, durability properties, etc. Preferred amounts of triazine in the polish composition have been found to be in the range from about 1 to 15 parts by weight triazine, preferably 1 to 5 parts by weight, based on 100 parts by weight of the wax composition (as used herein, the phrase "polish composition" stated in terms of parts by weight of materials therein refers to the base component(s), plus any solvent).

The fluorochemical triazines of the present invention are also useful as marine antifouling coating composition. Preferred compounds include those have a silane (or silanol) function groups, and it is further preferred that the ratio of fluorochemical groups to silane (or silanol) groups is in the range of 1:1 to 1:3. Preferably the fluorochemical triazine compounds are coated neat, but solvents may be used. When used, it is preferred that the solvent be water. When cured, the resulting coatings are durable in marine environments, exhibit low surface energies and, as result, provide surfaces from which marine fouling is readily removed.

Fouling refers to the accumulation of airborne or waterborne biological materials on surfaces. Marine surfaces are especially prone to fouling, due to the affinity of marine organisms for areas at or below the waterline. In marine environments, fouling involves surfaces on ship hulls, buoys, drilling platforms, pipes, and the like. Fouling build up on these surfaces can lead to a number of problems, such as increased weight or drag in the water, which, in the case of ships, can result in increased fuel consumption and operating costs.

The most common approach to prevention of marine fouling is through use of toxic antifouling coatings. The most commonly used antifouling coatings contain metallic toxicants, such as organo-tin or copper, which prevent marine organisms from attaching to the surface through release of the toxicant into the surrounding water. Such coatings may also contain an organic toxicant. A common form of these coatings, known as ablative antifouling coatings, wear away as the ship's hull passes through the water. This ablative action constantly brings fresh toxicant to the surface, until the toxicant concentration falls below a critical level, at which point the coating becomes ineffective. In order to restore the coating, the ship must be dry-docked and go through a recoating process.

A major concern of the use of antifouling coatings is the impact the leaching metallic toxicant poses to the environment. The use of organotin-based coatings has been found to kill, or at least severely restrict, the growth of marine life. This is especially true in areas of high ship traffic, such as harbors, bays, and estuaries. The use of copper based antifouling coatings is also being scrutinized for environmental hazards. It has been estimated that a ship having 3250 square meter hull area releases approximately 0.91 kg of copper per day, which is sufficient to bring approximately 18.9 million liters of sea water to toxic copper concentrations. ("Fluorinated Ship-Hull Coatings for Non-Polluting Fouling Control"; http://inel.gov/new/funding/serdp/p2prj005.html; May 30, 1996). Restrictions as to release of toxins into the environment are in place in certain areas. In addition to these problems, hulls coated with copper based coatings may experience the need for more frequent recoating than organotin-based coatings.

An alternative to the toxicant release approach is providing a coating or surface to which fouling organisms have difficulty adhering. Ideally, the turbulence created by the motion of the ship through water or simple cleaning methods would remove fouling organisms.

Pioneering work conducted by J. Griffith, "Nontoxic Alternatives to Antifouling Paints," *Journal of Coatings Technology*, vol 59 (755), 1987, pp 113–119, demonstrated that low surface energy coatings derived from fluoropolymers can function as fouling release coatings. Although these coatings demonstrated the principle of fouling release, certain marine organisms such as barnacles adhered strongly to the surface, requiring a cleaning step to remove them.

A. Beca and G. Loeb ("Ease of Removal of Barnacles from Various Polymeric Materials," *Biotechnical and Bioengineering*, v. 26, p. 1245–1251, 1984) studied the attachment of barnacles to a variety of polymeric surfaces and concluded that barnacles attached to a low surface energy surface were easier to remove than those attached to surfaces with higher surface energy. Researchers have also demonstrated through testing that marine organisms, in particular barnacles, attach more strongly to hard plastics than they do to soft elastomers.

A low surface energy approach was also demonstrated by Lindner, ("Low Surface Free Energy Approach In The Control of Marine Biofouling," *Biofouling*, 1992, Hardwood Academic Polyurethane Publishers, Vol. 99, pp. 193–205) who calculated coating surface energies based on contact angles with water and other liquids, and correlated them with contact angles critical to prevention of fouling by marine organisms. The higher the contact angle with water, the lower the surface energy of the coating surface. These materials were exemplified with oriented monolayers of perfluorinated surfactants fixed by polymers on the surface and by comb-like polymers with perfluorinated side chains.

These studies confirm the need for a low surface energy surface, but also indicate that other factors, such as low glass transition temperature ($<-20°$ C.) and elastomeric nature of the coating also play an important role in governing adhesion of marine organisms to polymeric surfaces.

Many commercially available silicones also contain leachable additives or residuals, which slowly move to the surface to form a weak boundary layer, resulting in easier removal of fouling organisms. Often, this additive is a silicone fluid.

While silicone coatings meet the requirements of low surface energy, low glass transition temperature, and elastomeric nature, there are major drawbacks to their use. These include poor abrasion resistance, tensile strength, and tear strength. These drawbacks result in susceptibility to mechanical damage. Also, silicone coatings do not exhibit good resistance to marine grasses and algae. Other potential problems with commercially available silicone fouling release coatings may include high solvent content and high applied cost. Application cost may be high due to the necessity of multiple coats of dissimilar layers in order to achieve acceptable adhesion. Many of the silicone products are multi-component, requiring on-site mixing and pot life concerns.

Teflon™ filled materials, such as epoxies and vinylesters, are available, but they have a high glass transition temperature, are non-elastomeric, and are not low enough in surface energy to prevent strong adhesion of marine fouling organisms.

This invention is illustrated by, but is not intended to be limited to, the following examples.

Test Procedure I—Repellency Rating

By this test, repellency was tested from an anti-graffiti standpoint. A Sharpie™ permanent marker was applied to the coated substrate being tested, drawing a line beginning on the uncoated area and proceeding on to the coated area. The repellency was visually rated by the following scale:

| Rating | Observation |
| --- | --- |
| 0 | Leaves permanent mark with no difference between the coated and uncoated areas |
| 1 | Slight narrowing of the drawn line in the coated area |
| 2 | Increased narrowing of the drawn line, resulting in streaks or dewetting in the coated area |
| 3 | Drawn line becomes discontinuous and results in a line of ink spots where the dewetted ink has separated into individual pools |

Test Procedure II—Contact Angle and Surface Energy Determinations

Surface energies were calculated using the software provided with the VCA 2000 Video Contact Angle System (AST Products, 9 Linnell Circle, Billerica, Mass. U.S.A. 01821)(Geometric Mean Method). Reported values are the average of the surface energy calculated from the contact angles of the testing liquids, water/formamide and water/methylene iodide pairs.

Combining the geometric-mean equation with Young's equation gives $$(1+\cos \Theta_1)\gamma_1 = 2[(\gamma_1{}^d\gamma_s{}^d)^{1/2} + (\gamma_1{}^p\gamma_s{}^p)^{1/2}] \quad \text{equation 1}$$

$$(1+\cos \Theta_2)\gamma_2 = 2[(\gamma_2{}^d\gamma_s{}^d)^{1/2} + (\gamma_2{}^p\gamma_s{}^p)^{1/2}] \quad \text{equation 2}$$

where the superscripts 1 (water, for example) and 2 (formamide, for example) refer to the testing liquids 1 and 2, respectively. When two testing liquids of known surface tension, $\gamma$, and its components are used to measure the contact angle, $\Theta$, equation 1 and 2 can be solved simultaneously to give $\gamma_s{}^d$ and $\gamma_s{}^p$. These are the dispersion and polar components of solid surface tension (*Polymer Interface and Adhesion*, p. 181, Marcel Dekker Inc., 1982, incorporated by reference herein).

Test Procedure III—Advancing and Receding Contact Angle Determination

Advancing and receding contact angles were determined in water (OmniSolv Water WX0004-1 from EM Science, 480 S. Democrat Rd, Gibbstown, N.J. 08027) using a Cahn Instruments DCA System™ at a speed of 80.00 microns/sec and an immersion depth of 8 mm. Values reported are the mean of three measurements. The DCA System is available from Cahn Instruments, 5225 Verona Road, Bldg. 1, Madison, Wis. 53711-4495. A description of dynamic contact angles is found in *Modern Approaches to Wettability Theory and Application*, p.332–333, Plenum Press, 1992.

EXAMPLES

Example 1

To a 12,000 ml flask equipped with a mechanical stirrer, reflux condenser, and nitrogen purge was added 600 grams (2.4 moles) of 2,4,6-triallyloxy-1,3,5-triazine (available from Sigma-Aldrich, Milwaukee, Wis.), 229.3 grams (2.16 moles) of 3-mercaptopropionic acid (available from Sigma-Aldrich, Milwaukee, Wis.), 2.5 grams of VAZO™ 64 (2,2'-azobisisobutyronitrile, available from Sigma-Aldrich, Milwaukee, Wis.), and 1412 grams of 4-methyl-2-pentanone (MIBK). The mixture was stirred to form a solution, and heated to 65° C. under a slight nitrogen purge. When an exotherm caused the temperature to rise to 85° C., the flask was cooled to 70° C. and held at this temperature for 18 hours. The solvent was then stripped from the reaction mixture at a temperature of 70° C. under aspirator vacuum.

The flask was then charged with 600 grams (1.05 moles) EtFOSE alcohol (available as FX-10 from 3M, St. Paul, Minn.), 308 grams (0.53 mole) FOSEE diol (prepared as described in Example 2 of U.S. Pat. No. 4,289,892), and 1.1 gram n-butylhydroxyoxostannane hydrate (available from Sigma-Aldrich, Milwaukee, Wis.). Under a positive nitrogen purge the mixture was heated with stirring to 170° C. and held at this temperature for 4 hours. The resulting liquid was cooled to a viscous oil which was dissolved in 3752 grams of MIBK. The solution was filtered to remove a trace of precipitate. To the filtered solution was added 940 grams (4.78 moles) of mercaptopropyltrimethoxysilane (available from Sigma-Aldrich, Milwaukee, Wis.) and 5 grams VAZO™ 64. The resulting solution was stirred and purged with nitrogen for 30 minutes, and then heated at 70° C. for 10 hours. The solution was then stripped of volatile material at a temperature of 70° C. under aspirator vacuum in a rotary evaporator to give a free flowing viscous oil product, containing an average of 22 mole % perfluorooctylsulfonamidoethyl thioether and 66 mole % trimethoxysilylpropyl thioether groups (in a 1:3 mole ratio) attached to one or more triazine ring(s) via oxypropyl links. The reported mole percent of each group is based on the total equivalents of attachment sites available.

Example 2

The product from Example 1 was mixed with 7 weight % titanium(IV) isopropoxide catalyst (available from Sigma-Aldrich, Milwaukee, Wis.) [dibutyltindiacetate catalyst, available from Sigma-Aldrich, Milwaukee, Wis., may also be used] based on total solids and coated with a number 7 Meyer rod onto the following unprimed substrates: polyester film, poly(methyl methacrylate) sheeting, polycarbonate sheeting, and polyvinylchloride sheeting. The coatings were cured at ambient temperature. After coating, the coatings were tack free in 15 minutes and completely cured in 1 hour. When rated for repellency according to Test Procedure I the coatings were all found to have a high level of repellency, with a repellency rating of 3.

Example 3

Preparation of $C_8F_{17}CH_2CH_2SH$: To a 12L flask equipped with a mechanical stirrer, a reflux condenser, Dean-Strark trap, and a nitrogen line, was added 2995 g of deionized water, and 2995 ML of dioxane. The resultant mixture was heated to 70° C. under nitrogen, and 2919.4 g of perfluorooctanesulfonyl fluoride (POSF) was added in one portion. The resulting mixture was heated at 70° C. for 9 hours. After this period, the mixture was cooled to 35° C. overnight, and the following morning the mixture was steam distilled to remove the unreacted POSF. There was about 194 g of POSF collected as the lower phase in the Dean-Strark trap. The remaining material in the flask was cooled, and 2995 g of deionized water, 540 g of aluminum potassium sulfate, and 730 g of sodium borate was added. As the resulting mixture was stirred at 50° C., 2175 g of iodine was added in portions with care to avoid foaming. This very viscous mixture could foam up easily at temperatures over 85° C. The product was steam distilled and collected as the lower phase in the Dean-Stark trap, and the excess iodine was reduced with aqueous sodium sulfite. The yield was about 2500 g of a colorless liquid 2-perfluorooctyl iodide.

Into a 2L 316 stainless steel Parr reactor, equipped with a mechanical stirrer, gas inlet tube and thermocouple, was placed the perfluorooctyl iodide (1220 g) and di-t-butyl peroxide (9.13 g). The reactor was cooled in Dry Ice, evacuated and ethylene (62 g) was initially charged to the reactor. The reactor was heated to 90° C. whereby the internal pressure decreased during the 16 hour reaction time. Additional ethylene (11 g) was added while the reaction was allowed to go to completion. A waxy white solid product (1225 g) was obtained after the reactor was cooled and excess pressure released. GLC analysis showed no unreacted perfluorooctyl iodide. GC/MS revealed less than 0.2% of 4-(perfluorooctyl)butyl iodide, the 1:2 adduct of the iodide and ethylene. The waxy material was used without further purification.

A mixture of thiourea (105.7 g, 1.39 moles), 2-(perfluorooctyl)ethyl iodide (531.5 g), 0.926 moles) and anhydrous ethanol (1000 mL) was heated at reflux for 6 hours. Approximately half of the alcohol was removed at reduced pressure and replaced with water. Solid sodium hydroxide (37.0 g) was added and the mixture heated under slow nitrogen purge. The volatile liquid products were collected by steam distillation using a modified Dean-Stark apparatus to yield 414 g (93.1 molar yield) of 2-(perfluorooctyl)ethyl mercaptan. After two consecutive water washes the product was suficiently pure by glc (99.3%) and used without further purification.

To a 1000 ml round bottom flask equipped with a mechanical stirrer, reflux condenser, and nitrogen purge was added 30 grams (0.12 mole) of 2,4,6-triallyloxy-1,3,5-triazine, 51.8 grams (0.11 mole) of 2-(perfluorooctyl)ethyl mercaptan, 48.4 grams (0.25 mole) mercaptopropyltrimethoxysilane, 1.5 grams of VAZO™ 64, and 353 grams of MIBK. The mixture was stirred to form a solution with a nitrogen purge, and heated to 70° C. under a slight nitrogen purge and held at this temperature for 18 hours. The solution was then stripped of volatile material at a temperature of 70° C. under aspirator vacuum in a rotary evaporator to give a free flowing viscous oil product containing an average of 31 mole % 2-(perfluorooctyl)ethyl thioether and 69 mole % trimethoxysilylpropyl thioether groups (in a 1:2.27 mole ratio) attached to a triazine ring via oxypropyl links. The reported mole percent of each group is based on the total equivalents of attachment sites available.

Example 4

The product from Example 3 was mixed with catalyst, coated and tested (using Test Procedure I) as in Example 2.

All of the coatings were found to have a high repellency and were given a repellency rating of 3.

Example 5

To a 5000 ml round bottom flask equipped with a mechanical stirrer, reflux condenser, and nitrogen purge was added 265.8 grams (1.07 moles) of 2,4,6-triallyloxy-1,3,5-triazine, 339.5 grams (3.19 moles) of mercaptopropionic acid, 4 grams of VAZO™ 64, and 1412 grams of MIBK. The mixture was stirred to form a solution with a nitrogen purge, and heated to 65° C. under a slight nitrogen purge. When an exotherm caused the temperature to rise to 85° C., the flask was cooled to 70° C. and held at this temperature for 16 hours. The solvent was then stripped from the reaction mixture at a temperature of 70° C. under aspirator vacuum in a rotary evaporator, producing the tris(carboxyethyl thioether) derivative as a viscous liquid.

To a 1000 ml round bottom flask equipped with a mechanical stirrer, reflux condenser, and nitrogen purge was added 50 grams (0.23 mole) of the tris(carboxyethyl thioether) derivative, 132.5 grams (0.46 mole) EtFOSE alcohol, 17.1 grams (0.06 mole) FOSEE diol, and 0.2 gram n-butylhydroxyoxostannane hydrate. Under a positive nitrogen purge the mixture was heated with stirring to 190° C. and held at this temperature for 2.7 hours. The resulting liquid was cooled to a viscous oil which was dissolved in 200 ml of ethyl acetate. The solution was filtered to remove a trace of precipitate. The ethyl acetate was stripped at a temperature of 70° C. under aspirator vacuum in a rotary evaporator. The resulting product was a viscous oil containing 84 mole % perfluorooctylsulfonamidoethyl thioetherpropionate and 16 mole % carboxyethyl thioether groups (in a 1:1.3 mole ratio) attached to one or more triazine ring(s). The reported mole percent of each group is based on the total equivalents of attachment sites available.

Example 6

The viscous oil product from Example 5 was mixed with a melamine in the following weight ratio: 1 part of the viscous oil from Example 5 was added to 4 parts of RESIMENE 747™ (available from Solutia Inc., formerly Monsanto, St. Louis, Mo.), followed by the addition of methanesulfonic acid at 7 weight % of the total mixture. This mixture was coated with a number 7 Meyer rod onto a polyester film and cured at 130° C. for 10 minutes to form a low surface energy top coating. When tested according to Test Procedure I a repellency of 1 was found.

Example 7

To a 5000 ml round bottom flask equipped with a mechanical stirrer, reflux condenser, and nitrogen purge was added 54.7 grams (0.93 mole) of the tris(carboxyethyl thioether) derivative of Example 5, 236.3 grams (0.41 mole) EtFOSE alcohol, 121.5 grams (0.21 mole) FOSEE diol, and 1.9 gram butyltin hydroxide oxide hydrate (n-butylhydroxyoxostannane hydrate). Under a positive nitrogen purge the mixture was heated with stirring to 170° C. and held at this temperature for 4 hours. The resulting liquid was cooled to a viscous oil which was dissolved in 1300 ml of ethyl MIBK. The solution was filtered to remove a trace of precipitate. The resulting solution was treated with 234.3 grams (1.64 mole) glycidyl methacrylate (available from Sigma-Aldrich, Milwaukee, Wis.) and 1.1 gram dimethylamino pyridine (available from Sigma-Aldrich, Milwaukee, Wis.) and heated at 117° C. for 18 hours. The MIBK was removed at 70° C. under aspirator vacuum in a rotary evaporator, to provide a viscous oil product containing 22 mole % perfluorooctylsulfonamidoethyl thioetherpropionate and 59 mole % 1-methacryloxy-2-hydroxypropyl thioetherpropionate groups (in a 1:2.26 mole ratio) attached to one or more triazine ring(s) via oxypropyl links. The reported mole percent of each group is based on the total equivalents of attachment sites available.

Example 8

The product of Example 7 was mixed with 3 weight % of IRGACURE™ 261 (available from Ciba Geigy Corp., Hawthorne, N.Y.) and coated onto a polyester film, using a number 7 Meyer rod. The coating was irradiated under a series of General Electric blacklight lamps for 1 hour and was then found to be still tacky. This sample failed to show any repellency when tested according to Test Procedure I.

Example 9

To a 1000 ml round bottom flask equipped with a mechanical stirrer, reflux condenser, and nitrogen purge was added 50 grams (0.20 mole) of triallyl-1,3,5-triazine-2,4,6 (1H,3H,5H)-trione (available from Sigma-Aldrich, Milwaukee, Wis.), 82.7 grams (0.172 mole) of 2-(perfluorooctyl)ethyl mercaptan, 85.9 grams (0.437 mole) mercaptopropyltrimethoxysilane, 2.5 grams of VAZO™ 64, and 510 grams of MIBK. The mixture was stirred to form a solution with a nitrogen purge, and heated to 70° C. under a slight nitrogen purge and held at this temperature for 18 hours. The solution was then stripped of volatile material at a temperature of 70° C. under aspirator vacuum to yield a free flowing viscous oil product containing an average of about 30 mole % 2-(perfluorooctyl)ethyl thioether and about 70 mole % trimethoxysilylpropyl thioether groups (in approximately a 1:2.5 ratio) attached to an isocyanurate ring. The reported mole percent of each group is based on the total equivalents of attachment sites available.

Example 10

The product from Example 9 was mixed with catalyst, coated and tested (using Test Procedure I) as in Example 2. The coatings were found to have a high level of repellency and given a repellency rating of 3.

Example 11

To a 5000 ml round bottom flask equipped with a mechanical stirrer, reflux condenser, and nitrogen purge was added 100 grams (0.40 mole) of triallyl-1,3,5-triazine- 2,4, 6(1H,3H,5H)-trione, 38.2 grams (0.36 mole) of mercaptopropionic acid, 4 grams of VAZO™ 64, and 1412 grams of MIBK. The mixture was stirred to form a solution with a nitrogen purge, and heated to 65° C. under a slight nitrogen purge. When an exotherm caused the temperature to rise to 85° C., the flask was cooled to 63° C. and held at this temperature for 20 hours. The solvent was then stripped from the reaction mixture at a temperature of 70° C. under aspirator vacuum. The flask was charged with 137 grams (0.24 mole) EtFOSE alcohol, 35.2 grams (0.06 mole) FOSEE diol, and 0.4 gram butyltin hydroxide oxide hydrate (n-butylhydroxyoxostannane hydrate). Under a positive nitrogen purge the mixture was heated with stirring to 170° C. and held at this temperature for 4.5 hours. The resulting liquid was cooled to a viscous oil which was dissolved in 576 grams of MIBK. The solution was filtered to remove a trace of precipitate. To the filtered solution was added 164.8 grams (0.84 mole) of mercaptopropyltrimethoxysilane and 3 grams VAZO™ 64. The resulting solution was stirred and purged with nitrogen for 20 minutes, and then heated at 70° C. for 10 hours. The solution was then stripped of volatile material at 70° C. under aspirator vacuum to yield a free flowing viscous oil product containing an average of 25 mole % perfluorooctylsulfonamidoethyl thioether and 70 mole % trimethoxysilylpropyl thioether groups (in a 1:2.8 mole ratio) attached to one or more isocyanurate ring(s) via a three carbon link. The reported mole percent of each group is based on the total equivalents of attachment sites available.

Example 12

The product from Example 11 was mixed with catalyst, coated, and tested (using Test Procedure I) as in Example 2. All coatings were found to have a high repellency and were given a repellency rating of 3.

Example 13

To a 250 ml round bottom flask equipped with a mechanical stirrer, reflux condenser, and nitrogen purge was added 15 g (0.056 mole) of 2,4,6-triallyloxy-1,3,5-triazine, 8.2 grams (0.055 mole) of mercaptosuccinic acid (available from Sigma-Aldrich, Milwaukee, Wis.), 0.5 grams of VAZO™ 64, and 64 grams of 2-butanone (MEK). The mixture was stirred to form a solution with a nitrogen purge, and heated to 65° C. under a slight nitrogen purge. The flask was held at this temperature for 16 hours. The solvent was then stripped from the reaction mixture at a temperature of 70° C. under aspirator vacuum in a rotary evaporator, producing a viscous liquid. To a 250 ml round bottom flask, the viscous oil was transferred and 38.6 g (0.105 mole) of N-methylperfluorobutylsulfonamidioethyl alcohol (which can be made from perfluorobutanesulfonyl fluoride, methylamine, and ethylene chlorohydrin using the procedures described in Example 1 of U. S. Pat. No. 2,803,656) was added followed by 2.0 grams (0.02 mole) of methanesulfonic acid (available from Sigma-Aldrich, Milwaukee, Wis.). The mixture was heated at 115° C. for 6.5 hours. The resulting dark oil was dissolved in 350 ml of MEK and filtered to remove any insoluble material. To the resulting MEK solution was added 24.1 grams (0.12 mole) mercaptopropyltrimethoxysilane, and the resulting solution was purged with $N_2$ and heated at 65° C. for 16 hours. The solution was then stripped of volatile material at 70° C. under aspirator vacuum in a rotary evaporator to give a free flowing viscous oil product containing and average of 47 mole % N-methylperfluorobutylsulfonamidoethyl thioether and about 53 mole % trimethoxysilylpropyl thioether groups (in a 1:1.1 mole ratio) attached to one or more triazine ring(s) via oxypropyl links. The reported mole percent of each group is based on the total equivalents of attachment sites available.

Example 14

The product from Example 13 was mixed with dibutyltindiacetate catalyst at 7 weight % based on total solids and coated with a number 7 Meyer rod onto polyester film. The coating was cured at ambient temperature. After coating, the sample was tack free in 40 minutes and completely cured in 3 hours. When evaluated according to Test Procedure I the repellency rating for the coating was found to be 1.

Example 15

To a 500 ml round bottom flask equipped with a mechanical stirrer, reflux condenser, and nitrogen purge was added 10 grams (0.05 equivalents of NCO) trimer of hexane diisocyanate (DESMODUR™ N-3300, available from Bayer Aktiengesellschaft, Leverkusen, Germany), 3.0 grams (0.05 mole) allyl alcohol, and 90 grams of MEK. The materials formed a solution with stirring and the solution was purged with $N_2$ for 5 minutes before being heated to 65° C. for 14 hours. To the room temperature solution was added 8 grams (0.05 mole) of mercaptosuccinic acid and 0.4 grams of VAZO™ 64. The solution was purged with $N_2$ for 5 minutes and heated at 65° C. for 12 hours. The solution was then stripped of volatile material at 70° C. under aspirator vacuum to give a free flowing viscous oil to which was added 11.8 grams (0.067 mole) of omega-undecylenyl alcohol and 12.8 grams (0.035 mole) N-methylperfluorobuthylsulfonamidoethyl alcohol and 0.3 grams of methanesulfonic acid.

The flask was heated at 115° C. for 6.5 hours and the resulting oil was allowed to cool before being dissolved in 180 ml of ethyl acetate. The solution was treated with 13.3 grams (0.067 mole) mercaptopropyltrimethoxysilane and 0.3 grams of VAZO™ 64, and purged with $N_2$ for 5 minutes before heated for 12 hours to give a uniform solution, containing product having an average of about 33 mole % N-methylperfluorobutylsulfonamidoethyl thioether and 67 mole % trimethoxysilylpropyl thioether groups (in a 1:1.9 mole ratio) attached to an isocyanurate ring via urethane links. The reported mole percent of each group is based on the total equivalents of attachment sites available.

Example 16

The product from Example 15 was mixed with a dibutyltindiacetate catalyst at 7 weight % based on total solids and coated by number 7 Meyer rod onto polyester film. The coating was cured at ambient temperature. After coating, the sample was tack free in 40 minutes and completely cured in 3 hours. When evaluated according to Test Procedure I the repellency rating for the coating was found to be 1.

Example 17

To a 500 ml round bottom flask equipped with a mechanical stirrer, reflux condenser, and nitrogen purge was added 10 grams (0.05 equivalent of NCO) trimer of hexane diisocyanate (Desmodure N-3300), 3.0 grams (0.05 mole) allyl alcohol, and 90 grams of MEK. The materials formed a solution with stirring, and the solution was purged with $N_2$ for 5 minutes before being heated to 65° C. for 14 hours. To the room temperature solution was added, 8 grams (0.05 mole) of mercaptosuccinic acid and 0.4 gram of VAZO™ 64. The solution was purged with $N_2$ for 5 minutes and heated at 65° C. for 12 hours. The solution was then stripped of volatile material at 70° C. under aspirator vacuum to yield a free flowing viscous oil to which was added 6.3 grams (0.036 mole) of omega-undecylenyl alcohol and 25.6 grams (0.066 mole) N-methylperfluorobutylsulfonamidoethyl alcohol and 0.3 gram of methanesulfonic acid.

The flask was heated at 115° C. for 6.5 hours and the resulting oil was allowed to cool before being dissolved in 180 ml of ethyl acetate. The solution was treated with 7.1 grams (0.036 mole) mercaptopropyltrimethoxysilane and 0.3 grams of VAZO™ 64 and then purged with $N_2$ for 5 minutes, followed by heating at 70° C. for 12 hours to give a uniform solution, containing product having an average of about 65 mole % N-methylperfluorobutylsulfonamidoethyl thioether and 35 mole % trimethoxysilylpropyl thioether groups (in a 1:0.55 mole ratio) attached to an isocyanurate ring via urethane links. The reported mole percent of each group is based on the total equivalents of attachment sites available.

Example 18

The product from Example 17 was evaluated as in Example 16 and found to have a repellency rating of 1. After coating, the sample was found to be tack free in 40 minutes and completely cured in 3 hour.

Comparative Example 1

To a 500 ml round bottom flask equipped with a mechanical stirrer was added 20 grams (0.083 mole) of 2,4,6-triallyloxy-1,3,5-triazine, 46.7 grams (0.082 mole) EtFOSE alcohol and 4.6 grams (0.082 mole) sodium methoxide (available from Sigma-Aldrich, Milwaukee, Wis.). The flask was heated at 115° C. for 4 hours. The resulting material was dissolved in 300 grams of ethyl acetate and washed with 50 grams of water. The layers were split and the organic layer was dried with stirring over $MgSO_4$. To the resulting solution was added 32.6 grams (0.166 mole) mercaptopropyltrimethoxysilane and 0.6 grams of VAZO™ 64, followed by purging with $N_2$ for 5 minutes. The final solution was heated at 65° C. for 12 hours. The resulting solution was stirred and purged with nitrogen for 30 minutes, and then heated at 70° C. for 10 hours. The solution was then stripped of volatile material at 70° C. under aspirator vacuum to yield a free flowing viscous oil product, which solidified upon cooling. This product contained on average 33 mole % N-ethylperfluorooctylsulfonamidoethyl ether and 67 mole % trimethoxysilyipropyl thioether groups (in a 1:2 mole ratio) attached to a triazine ring via oxypropyl groups. The reported mole percent of each group is based on the total equivalents of attachment sites available.

Comparative Example 2

A portion of the product from Comparative Example 1 was dissolved in ethyl acetate at 25 weight % based on total weight, and dibutyltindiacetate catalyst was mixed in at 7 weight % based on total solids. The solution was coated with a number 7 Meyer rod onto polyester film and cured at ambient temperature. After coating, the sample was tack free in 40 minutes and completely cured in 2 hour. The final film was hazy and showed poor repellency (0) to the permanent marker when tested according to Test Procedure I.

Example 19 and Comparative Example 3

Titanium (IV) isopropoxide was mixed with the product from Example 1 at 5% by weight of the total mixture. Twenty milled fiberglass rods having a diameter of 7 mm and a length of 110 mm were dipped into the resulting solution and allowed to cure at room temperature for seven days. The surface energy of the coated rods was determined according to Test Procedure II, and the result is shown in Table 1. Advancing and receding contact angles in deionized water were also measured according to Test Procedure III, and the results are shown in Table 1. The coated rods along with a corresponding number of uncoated rods (Comparative Example 3) were tested at Duke University Marine Laboratories (Beaufort, N.C.) for marine fouling according to the methods described by D. Rittshcof et al in *Biofouling*, 1992, Vol. 6, pp. 181–192. The weights of marine fouling before and after washing with the Water Pik™ are shown in Table 1.

Example 20

Titanium (IV) isopropoxide was added at 5 weight % to product made as in Example 11 and evaluated as in Example 19. The results are shown in Table 1.

Example 21

Titanium (IV) isopropoxide was added at 5 weight % to product made as in Example 3 and evaluated as in Example 19. The results are shown in Table 1.

Example 22

To a 2000 ml round bottom flask equipped with a mechanical stirrer, reflux condenser, and nitrogen purge was added 96.4 grams (0.387 mole) of 2,4,6-triallyloxy-1,3,5-triazine, 278.4 grams (0.58 mole) of 2-(perfluorooctyl)ethyl mercaptan, 113.8 grams (0.58 mole) mercaptopropyltrimethoxysilane, 5.3 grams of VAZO™ 64, and 1192 grams of MIBK. The mixture was stirred to form a solution with a nitrogen purge, and heated to 63° C. under a slight nitrogen purge and held at this temperature for 15 hours. A second charge of 2.5 grams VAZO™ 64 was added and heating continued for 24 hours. The solution was then stripped of volatile material at 70° C. under aspirator vacuum to yield a free flowing viscous oil product containing an average of 50 mole % 2-(perfluorooctyl)ethyl thioether and 50 mole % trimethoxysilylpropyl thioether groups (in a 1:1 mole ratio) attached to a triazine ring via oxypropyl links. The reported mole percent of each group is based on the total equivalents of attachment sites available. This is similar to that made in Example 3, except that the perfluorooctyl group content is higher, and the trimethoxysilyl content is lower than in Example 3. Titanium (IV) isopropoxide was added at 5 weight % to a portion of the product, and the resulting mixture was evaluated as in Example 19. The results are shown in Table 1.

Example 23

To a 5000 ml round bottom flask equipped with a mechanical stirrer, reflux condenser, and nitrogen purge was added 222.8 grams (0.894 mole) of 2,4,6-triallyl-1,3,5-triazine-2,4,6(1 H,3H,5H)-trione, 259.2 grams (0.540 mole) of 2-(perfluorooctyl)ethyl mercaptan, 245.4 grams (1.25 moles) mercaptopropyltrimethoxysilane, 7.3 grams of VAZO™ 64, and about 1700 grams of MIBK. The mixture was stirred to form a solution with a nitrogen purge, and heated to 63° C. under a slight nitrogen purge and held at this temperature for 14 hours. A second charge of 2.5 grams VAZO™ was added under $N_2$, and heating was resumed for 5 hours. The solution was then stripped of volatile material at 70° C. under aspirator vacuum to yield a free flowing viscous oil product containing an average of about 20 mole % 2-(perfluorooctyl)ethyl thioether and 47 mole % trimethoxysilylpropyl thioether groups (in a 1:2.3 mole ratio) attached to an isocyanurate ring. This is similar to that made in Example 9 except that the trimethoxysilyl group content is higher and the perfluorooctyl group content is lower than Example 9. Titanium (IV) isopropoxide was added at 5 weight % to a portion of the product, and the resulting mixture was evaluated as in Example 19. The results are shown in Table 1.

Example 24

To a 1000 ml round bottom flask equipped with a mechanical stirrer, reflux condenser, and nitrogen purge was added 15 g (0.0077 mol) of a n-propyl mercaptan functional dimethylsilicone (KF2001™, available from Shin-Etsu Chemical Co., Tokyo, Japan), 30 grams (0.12 mole) of 2,4,6-triallyloxy-1,3,5-triazine, 51.8 grams (0.11 mole) of perfluoroctylethylmercaptan, 48.4 grams (0.25 mole) mercaptopropyltrimethoxysilane, 2 grams of VAZO™ 64, and 317 grams of MIBK. The mixture was stirred to form a solution with a nitrogen purge, and heated to 70° C. under a slight nitrogen purge and held at this temperature for 18 hours. The solution was then stripped of volatile material at a temperature of 70° C. under aspirator vacuum in a rotary evaporator to give a free flowing viscous oil product containing on average 30 mole % perfluorooctylethyl thioether, 1 mole % dimethylsilicone, and 69 mole % trimethoxysilylpropyl thioether groups (a molar ratio of 1:0.033:2.3) attached to a triazine ring. Titanium(IV) isopropoxide was added at 5 weight % to a portion of the product, and the resulting mixture was evaluated for surface energy, advancing contact angle, and receding contact angle as in Example 19. The results are shown in Table 1.

TABLE 1

| Example | Surface Energy | Advancing Contact Angle[1] | Receding Contact Angle[2] | Weight of Marine Fouling Before Wash | Weight of Marine Fouling After Wash | % Fouling Remaining |
| --- | --- | --- | --- | --- | --- | --- |
| C3 | NR[3] | NR | NR | 2.05 g | 0.12 g | 5.9 |
| 19 | 16.4 | 94 | 65 | 2.2 g | 0.01 g | 0.45 |
| 20 | 18.6 | 100 | 59 | 11.0 g | 1.00 g | 9.0 |
| 21 | 14.9 | 101 | 69 | 2.3 g | 0.01 g | 0.43 |
| 22 | 12.8 | 111 | 62 | 3.3 | 0.2 | 0.61 |
| 23 | 18.1 | 92 | 71 | 2.3 | 0.15 | 6.5 |
| 24 | 18.2 | 108.9 | 84.2 | NR | NR | NR |

[1]Advancing Contact Angle in degrees.
[2]Receding contact Angle in degrees.
[3]NR = not run.

Table 1 shows that the ease of removing the marine fouling from the surface of the coated rod is increased as the surface energy of the rod's surface is decreased and as the combination of advancing and receding contact angles is increased. It is expected that fouling on boat hulls and other movable marine structures will come off when moved through the water when coatings, such as those in Examples 19, 21, and 22 (which showed excellent fouling removal in the above test) are present.

Comparative Example 4—Liquid Wax for Automotive and Marine Protective Coatings The liquid wax used as a control (without fluorinated triazines in comparative example C4) and also used with fluorinated triazine of the present invention (in Examples 25–29 is a modified formulation taken from Dow Corning's *Automotive Car Formulation Guide* form no. 25-653-94, formulation APF 310. (Dow Corning Corporation, Midland, Mich.).

Water (60.00 grams) was mixed with 10.00 grams of Kaopolite™ SF (Kaopolite, Inc., Union, N.J.). To the stirred mixture, 1.00 gram of Witcamide™ 511 (Witco Corporation, Houston, Tex.), and 21.50 grams of Stoddard solvent was added. Once uniform, 6.00 grams of Dow Corning™ 531 Fluid and 1.00 gram of Dow Corning™ 536 Fluid was added (both from Dow Corning Corporation, Midland, Mich.), followed by 0.50 grams of Bentone™ 38 (Rheox Corporation, Highstown, N.J.) and the mixture was stirred until uniform. The resulting liquid wax (0.5 grams) was coated on an ACT Black OEM clear coated panel No. AIN78436 (obtained from ACT Laboratories, Inc. of Hillside, Mich.) and allowed to haze (evaporate slowly) until solvent evaporation was complete. The coating was rubbed by hand using a soft cloth, and the panel was placed in a 120° F. oven for 24 hours.

Contact angle measurements were taken on the panel according to Test Procedure II. The panel was then subjected to abrasion with a ScotchBrite™ "T" type pad (available from 3M, St. Paul, Minn.) with a five pound weight using 50 grams of a concentrated (50:1) solution of 3M Car Wash Soap (available from 3M, St. Paul, Minn.) as a lubricant. The panel was abraded in 500 cycle intervals on a BYK-Gardener Abrasion Tester (available from Byk-Chemie, Wallingford, Conn., USA), and the static contact angle of water on the panel surface was measured using Test Procedure II after each 500 cycle interval. All contact angle results are shown in Table 2.

Example 25

To the liquid wax described in Comparative Example 4 was added 10% by weight of the fluorochemical triazine composition of Example 11. After high shear mixing, the resulting composition was applied to an OEM panel and subjected to contact angle testing before and after abrasion as in Comparative Example 4. The results are shown in Table 2.

Example 26

The fluorochemical triazine composition of Example 3 was mixed with liquid wax and tested as in Example 25. The results are shown in Table 2.

Example 27

A portion of the product made in Example 22 was mixed with liquid wax and tested as in Example 25. The results are shown in Table 2.

Example 28

A portion of the product made in Example 23 was mixed with liquid wax and tested as in Example 25. The results are shown in Table 2.

Example 29

To a 2000 ml round bottom flask equipped with a mechanical stirrer, reflux condenser, and nitrogen purge was added 100 grams (0.40 mole) of 2,4,6-triallyloxy-1,3,5-triazine, 144 grams (0.30 mole) of 2-(perfluorooctyl)ethyl mercaptan, 164.9 grams (0.84 mole) mercaptopropyltrimethoxysilane, 115.9 grams (0.06 mole) mercapto-functional polydimethylsiloxane ( available as KF20001 from Shin-Etsu Chemical Co., Tokyo, Japan), 5.2 grams of VAZO™ 64, and 1225 grams of MIBK. The mixture was stirred with a nitrogen purge, and heated to 63° C. under a slight nitrogen purge and held at this temperature for 12 hours. A second charge of 2.2 grams VAZO™ 64 was added and heating continued for 5 hours. The solution was then stripped of volatile material at a temperature of 70° C. under aspirator vacuum in a rotary evaporator to give a cloudy product, which separated on standing. The product contained 2-(perfluorooctyl)ethyl thioether, trimethoxysilylpropyl thioether, and polymethylsiloxane thioether groups (in a 1:2.8:0.2 mole ratio) attached to a triazine ring via oxypropyl links. A portion of the product was mixed with liquid wax and tested as in Example 25. The results are shown in Table 2.

TABLE 2

| | Water Contact Angle After Indicated Number of Abrasion Cycles | | | | | | | |
|---|---|---|---|---|---|---|---|---|
| Example | 0 | 500 | 1000 | 1500 | 2000 | 2500 | 3000 | 3500 |
| C4 | 99.3 | 87.6 | 74.3 | 72.1 | 71.6 | 70.9 | 69.8 | 68.7 |
| 25 | 101.3 | 97.8 | 95.3 | 95.8 | 96.0 | 94.3 | 92.5 | 91.3 |
| 26 | 96.3 | 92.5 | 89.3 | 84.8 | 85.3 | 78.0 | 81.0 | 81.3 |
| 27 | 96.0 | 96.3 | 95.8 | 86.5 | 88.5 | 82.3 | 82.0 | 81.0 |
| 28 | 94.0 | 87.8 | 82.0 | 83.0 | 80.3 | 80.3 | 78.3 | 75.8 |
| 29 | 96.0 | 92.8 | 85.5 | 85.3 | 84.8 | 85.8 | 80.5 | 80.8 |

The results in Table 2 clearly show that the addition of the fluorochemical triazine compositions of the present invention to the liquid wax formulation enhances the durability of the wax when challenged with abrasion.

Examples 30–32 and Comparative Examples C5–C7

A free flowing viscous oil product containing an average of about 20 mole % 2-(perfluorooctyl)ethyl thioether and 47 mole % trimethoxysilylpropyl thioether groups (in a 1:2.3 mole ratio) attached to a triazine ring was made as described in Example 23, except that 2,4,6-triallyloxy-1,3,5-triazine was used in place of the trione. The product was mixed with dibutyltindiacetate catalyst at 7 weight % based on total weight and coated onto 3M Scotchlite™ Removeable Reflective Sheeting (690 Sheeting), 3M 3870 Silver Scotchlite™ High Intensity Sheeting (HIS White), and 3M 3970 White Scotchlite™ Diamond Grade Sheeting (DG White) (all available from 3M, St. Paul, Minn.) using a No. 10 Meyer bar. The coatings were allowed to cure at ambient temperature for at least one hour, and were then tested for contact angle. Contact angle was determined by placing each coated sheet (adhered to a flat, aluminum panel) in a horizontal position. Using a syringe attached to a micrometer, a drop of deionized water was carefully allowed to form as a droplet on the surface location of the sheeting to be tested. The elevation of the plate was then adjusted so that the eyepiece of a NRL C.A. Goniometer (Model 100-00, Ramehart, Inc., Mountain Lakes, N.J.) was level with the plane of the plate. The baseline of the goniometer was then set to correspond with the plane of the plate. The eyepiece was then rotated until the eyepiece line was tangent to the drop and the internal angle was recorded as the contact angle. Uncoated sheets also mounted on flat, aluminum panels were similarly tested for contact angle. All results are shown in Table 3.

Examples 33–35

Product made according to Example 23 was mixed with dibutyltindiacetate catalyst at 7 weight % based on total weight, and coated onto 3M Scotchlite™ Removeable Reflective Sheeting (690 Sheeting), 3M 3870 Silver Scotchlite™ High Intensity Sheeting (HIS White), and 3M 3970 White Scotchlite™ Diamond Grade Sheeting (DG White) (all available from 3M, St. Paul, Minn.) using a No. 10 Meyer bar. The coatings were allowed to cure at ambient temperature for at least one hour, and were then tested for contact angle as in Examples 30–33. Results are shown in Table 3.

TABLE 3

| Sheeting | Example | Contact Angle | Comparative Example | Contact Angle |
|---|---|---|---|---|
| 690 | 30 | 104 | C5 | 72 |
| HIS White | 31 | 109 | C6 | 67 |
| DG White | 32 | 108 | C7 | 71 |
| 690 | 33 | 111 | | |
| HIS White | 34 | 112 | | |
| DG White | 35 | 110 | | |

The results in Table 3 demonstrate a substantial increase in the repellency of reflective sheetings as seen by contact angle and beading of the water on the surface because of the coatings of the present invention.

Example 36

To a 250 ml round bottom flask equipped with a mechanical stirrer, reflux condenser, and nitrogen purge was added 15 grams (0.056 moles) of 2,4,6-triallyloxy-1,3,5-triazine, 8.2 grams (0.53 moles) of mercaptosuccinic acid, 0.5 grams of VAZO™ 64, and 64 grams of MEK. The mixture was stirred to form a solution with a nitrogen purge, and heated to 65° C. under a slight nitrogen purge. The flask was held at this temperature for 16 hours. The solvent was then stripped from the reaction mixture at a temperature of 70° C. under aspirator vacuum in a rotary evaporator, producing a viscous liquid. To a 250 ml round bottom flask the viscous oil was transferred, and 53 grams (0.105 moles) of Zonyl™ BA—L ($R_fCH_2CH_2OH$, where $R_f$ includes a mixture of $C_4F_9$—, $C_6F_{13}$—, $C_8F_{17}$—, and $C_{10}F_{21}$— groups, and available from Du Pont Co., Wilmington Del.) alcohol was added followed by 2.0 grams (0.02 moles) of methanesulfonic acid. The mixture was heated at 115° C. for 6.5 hours. The resulting dark oil was dissolved in 350 ml of MEK and filtered to remove any insoluble material. To the resulting MEK solution was added 24.1 grams (0.12 moles) mercaptopropyltrimethoxysilane. The resulting solution was purged with $N_2$ and heated at 65° C. for 16 hours. The solution was then stripped of volatile material at a temperature of 70° C. under aspirator vacuum in a rotary evaporator to give a free flowing viscous oil product that solidified on cooling. The sample contained on average 33 mole % (perfluoroalkyl) ethyl thioether groups and 66 mole % trimethoxysilylpropyl thioether groups attached a triazine ring(s) via oxypropyl links.

Example 37

The fluorochemical triazine product from Example 36 was dissolved in ethyl acetate at 10 weight % based on the total weight, and dibutyltindiacetate catalyst dissolved in the resulting solution at 7 weight % based on total solids. The solution was coated onto a polyester film using a No. 7 Meyer bar. The coating was cured at 125° C. for 15 min. When rated for repellency according to Test Procedure I the coating was found to have a repellency rating of 1.

Example 38

A 1% solution of the fluorochemical triazine of Examples 30–32 was prepared by dissolving 4.77 grams of the product and 0.095 gram titanium(IV) isopropoxide in 472 grams of ethyl acetate. A portion (35 grams) of the resulting solution was applied to a 25.4 cm by 30.5 cm (35 grams) swatch of Red Emperor Stretch 100% polyester velvet automotive upholstery fabric (available from Collins and Aikman Co., Roxboro, N.C.) by pad application. The padder (Model 93-1244 available from Aztec Machinery Co., Ivyland, Pa.) was set at 0.414 MPa (60 psi) and 6.1 m/min. (20 ft./min.). The resulting padded fabric was hung in a forced air oven at 154° C. for 10 minutes. After cooling to room temperature the padded fabric was tested for oil and water repellency using 3M Oil Repellency Test I and 3M Water Repellency Test II: Water/Alcohol Drop Test (both written test methods available from 3M Protective Materials Division, St. Paul, Minn.). Two small pieces of padded fabric were tested to determine the amount of fluorine present using 3M Fluorine Analysis Combustion Test (available from 3M Protective Materials Division, St. Paul, Minn.), and the average of the results from the two samples is shown in Table 4. Portions of the padded fabric were separately subjected to 2000, 8000, and 16,000 cycles of Stoll abrasion and then tested for oil and water repellency as above. Stoll abrasion was done by first dimensioning a circular piece of padded fabric to fit the surface abrasion platform of a Stoll Abrader (Model CS-59 available from Custom Scientific Instruments, Cedar Knolls, N.J.). The padded fabric was placed on the abrasion platform, and a new piece of abradant fabric (100% cotton Duck fabric, also known as unbleached Twill, 339 g/m$^2$) was placed in the abradant holder above the padded fabric specimen. A 2.27 Kg (5 lb.) weight was place on top of the abradant fabric holder. After setting the abrader for the desired number of cycles it was started, and after completion of the cycles, the fabric was removed for testing. Results are shown in Table 4.

Example 39

A 2% solution of the fluorochemical triazine of Examples 30–32 was prepared by dissolving 4.77 grams of the product and 0.095 gram titanium(IV) isopropoxide in 230 grams of ethyl acetate. The resulting solution was applied to Red Emperor Stretch 100% polyester velvet fabric as in Example 38. Oven treatment and testing of the padded fabric was conducted as in Example 38. Results are shown in Table 4.

Example 40

A 4% solution of the fluorochemical triazine of Examples 30–32 was prepared by dissolving 4.77 grams of the product and 0.095 gram titanium(IV) isopropoxide in 114.5 grams of ethyl acetate. The resulting solution was applied to Red Emperor Stretch fabric as in Example 38. Oven treatment and testing of the padded fabric was conducted as in Example 38. Results are shown in Table 4.

Example 41

A 1% solution of the fluorochemical triazine of Examples 30–32 was prepared by dissolving 4.77 grams of the viscous oil product and 0.095 gram titanium(IV) isopropoxide in 472 grams of ethyl acetate. A portion (33 grams) of the resulting solution was applied to a 25.4 cm by 30.5 cm (32.8 grams) swatch of Red Dorchester 100% polyester velvet automotive upholstery fabric (available from Collins and Aikman Co., Roxboro, N.C.) as in Example 38. Oven treatment and testing of the padded fabric was conducted as in Example 38. Results are shown in Table 4.

Example 42

A 2% solution of the fluorochemical triazine of Examples 30–32 was prepared by dissolving 4.77 grams of the viscous oil product and 0.095 gram titanium(IV) isopropoxide in 230 grams of ethyl acetate. A portion (33 grams) of the resulting solution was applied to a 25.4 cm by 30.5 cm (32.8 grams) swatch of Red Dorchester 100% polyester velvet automotive upholstery fabric (available from Collins and Aikman Co., Roxboro, N.C.) as in Example 38. Oven treatment and testing of the padded fabric was conducted as in Example 38. Results are shown in Table 4.

Example 43

A 4% solution of the fluorochemical triazine of Examples 30–32 was prepared by dissolving 4.77 grams of the viscous oil product and 0.095 gram titanium(IV) isopropoxide in 114.5 grams of ethyl acetate. A portion (33 grams) of the resulting solution was applied to a 25.4 cm by 30.5 cm (32.8 grams) swatch of Red Dorchester 100% polyester velvet automotive upholstery fabric (available from Collins and Aikman Co., Roxboro, N.C.) as in Example 38. Oven treatment and testing of the padded fabric was conducted as in Example 38. Results are shown in Table 4.

Comparative Example C8

A protective fluorochemical emulsion, FX-259™ (available from 3M, St. Paul, Minn. for providing oil and water repellency to automotive fabrics), was prepared by diluting 22.7 grams of FX-259™ to a volume of one liter by the addition of water. A portion (23.1 grams) of the resulting mixture was applied to a 25.4 cm by 30.5 cm (32.8 grams) swatch of Red Dorchester 100% polyester velvet automotive upholstery fabric (available from Collins and Aikman Co., Roxboro, N.C.) as in Example 38. Oven treatment and testing of the padded fabric was conducted as in Example 38. Results are shown in Table 4.

TABLE 4

| Example | Fluorine (ppm) | Oil/Water Repellency Ratings | | | |
|---|---|---|---|---|---|
| | | 0 Cycles | 2K Cycles | 8K Cycles | 16K Cycles |
| 38 | 2010 | 4/3 | 4/3 | 1/2 | 0/1 |
| 39 | 4539 | 4/4 | 4/3 | 2/3 | 1/2 |
| 40 | 7033 | 4/5 | 4/4 | 4/4 | 3/3 |
| 41 | 1800 | 4/4 | 4/3 | 2/3 | 1/3 |
| C8 | 1784 | 7/10 | 6/7 | 2/4 | 0/2 |
| 42 | 3222 | 4/5 | 4/3 | 3/3 | 2/3 |
| 43 | 7680 | 4/5 | 4/3 | 4/3 | 3/3 |

The results in Table 4 show that the fluorochemical triazine provides repellency proved durability compared with known fabric repellency treatments.

What is claimed is:

1. A fluorochemical triazine compound of the formula:

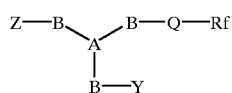

where A is a triazine ring of the formula

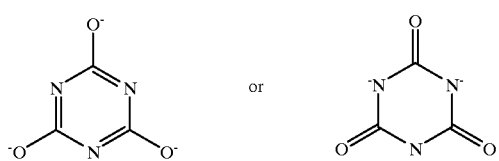

wherein
each B is an oxalkylene, azaalkylene or thiaalkylene moiety, each Q is a divalent linking group,
$R_f$ is a flourinated aliphatic group,
Y is a functional group capable of undergoing a displacement reaction, or capable of undergoing free-radical polymerization,
Z is —Q—$R_f$ or Y.

2. The fluoroaliphatic triazine of claim 1 selected from the group consisting of:

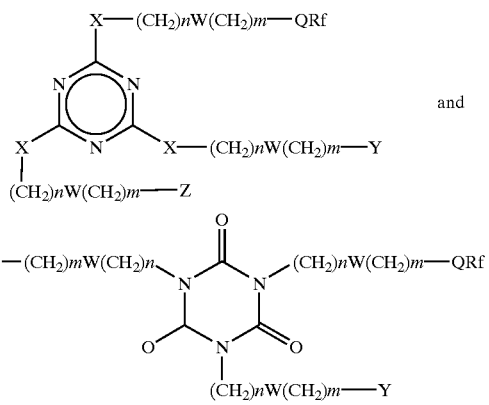

where each X is an oxygen or alkylamino of the formula —NR—, each W is an oxygen, sulphur or alkylamino of the formula —NR'—, where R is a lower alkyl, each n and m is independently an integer of from 1 to 20, Q is a divalent linking group, Y is a reactive functional group, $R_f$ is a fluoroaliphatic radical, and Z is $R_f$ or Y.

3. The fluoroaliphatic triazine compounds of claim 1 comprising compounds of the formula

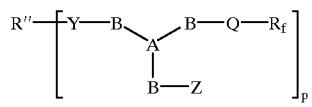

where Y, B, A, Q, Rf and Z are as defined in claim 1, R" is aliphatic moiety derived from a polyfunctional compound of functionality p, and p is a number from 2 to 4.

4. Coating compositions comprising the fluorochemical triazine of claim 1, further comprising a polymeric binder.

5. The coating composition of claim 4 wherein said binder is selected from the group of as phenolic resins, urethane resins, urea-formaldehyde resins, melamine and melamine-formaldehyde resins, epoxy resins, alkyd resins, amino resins and acrylate resins.

6. The coating composition of claim 4 further comprising a solvent.

7. The triazine compounds of claim 2 wherein each n and m are independently 2 to 12.

8. The triazine compounds of claim 2 wherein $R_f$ is a perfluoroaliphatic radical having 4 to 12 carbon atoms.

9. A polymer composition comprising the fluorochemical triazine compounds of claim 1 and a melt-processible polymer.

10. The polymer composition of claim 9 wherein said melt-processible polymer is selected from the group of linear polyamides, polyesters, polyurethanes, epoxides, acrylics, polystyrenes and polyolefins.

11. The polymer composition of claim 9 wherein said melt-processible polymer is selected from the group polyethylene and polypropylene.

12. A shaped article comprising the polymer composition of claim 9.

13. The shaped article of claim 12 selected from the group of fibers and films.

14. A surface treatment for fibrous substrates comprising a solution or dispersion of the fluorochemical triazine compounds of claim 1.

15. The fluorochemical triazine of claim 1 comprising compounds of the formula:

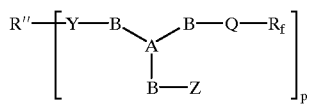

where B, A, Q, $R_f$ and Z are as defined in claim 1,
Y is a functional group,
and R" is derived from a polyfunctional compound of functionality p, and p is a number from 2 to 4 inclusive, said functional groups of said polyfunctional compound being co-reactive with functional group Y.

16. The triazine compounds of claim 15 wherein R" comprises an aliphatic chain of 2 to 20 carbon atoms.

17. The triazine compounds of claim 15 wherein p is 2.

18. The triazine compounds of claim 15 wherein R" comprises an fluorinated aliphatic chain of 4 to 12 carbon atoms.

19. A surface treated substrate comprising a cured coating of fluorochemical triazine of claim 1.

20. The surface treated substrate of claim 19 wherein said substrate is selected from glass, wood, stone, tile, grout, concrete, metal, fiberglass, and plastic substrates.

21. A surface treated substrate comprising a cured coating composition of claim 4.

22. A polish composition comprising the fluorochemical triazine compounds of claim 1 and a binder.

23. The polish composition of claim 22 wherein said binder comprises a wax or silicone oil.

24. The fluorochemical triazine compounds of claim 2 wherein the ratio of fluorochemical groups to functional groups is from 3:1 to 1:3.

25. A marine antifouling coating composition comprising the fluorochemical triazine of claim 1.

26. The antifouling coating composition of claim 25 wherein the functional group Y is a silane functional group.

27. A marine antifouling coating comprising the cured coating composition of claim 21.

28. The fluorochemical compounds of claim 1 wherein the moiety —Q—Rf is of the formula —S—$(CH_2)_n R_f$, wherein n is an integer of 1 to 5.

29. The fluorochemical triazine of claim 1, wherein Q is selected from the group consisting of a covalent bond, a divalent aliphatic group, a divalent aromatic group, an oxy group, a thio group, a carbonyl group, a sulfone group, a sulfoxy group, a —$N(CH_3)$— group, a sulfonamido group, a carbonamido group, a sulfonamidoalkylene group, a carbonamidoalkylene group, a carbonyloxy group, a urethane group, a urylene group, and combinations thereof.

30. The fluorochemical triazine of claim 1, wherein said Y groups that undergo displacement reactions are selected from hydroxyl, amino, azlactyl, oxazolinyl, 3-oxobutanoyl, carboxyl, ester, isocyanato, epoxy, aziridinyl, acyl halide, vinyloxy, silane, silanol and anhydride groups.

31. The fluorochemical triazine of claim 1, wherein said Y groups that undergo displacement reactions are selected from alkane, alkene, (meth)acrylate and vinyl ether groups.

* * * * *